(12) United States Patent
Wolter et al.

(10) Patent No.: US 9,206,205 B2
(45) Date of Patent: Dec. 8, 2015

(54) HYDROLYSABLE AND POLYMERIZABLE SILANES WITH ADJUSTABLE SPATIAL DISTRIBUTION OF THE FUNCTIONAL GROUPS, AND USE THEREOF

(71) Applicant: Fraunhofer-Gesellschaft zur Foerderung der angewandten Forschung e.V., Munich (DE)

(72) Inventors: Herbert Wolter, Tauberbischofsheim (DE); Somchith Nique, Eisingen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 14/346,591

(22) PCT Filed: Sep. 24, 2012

(86) PCT No.: PCT/EP2012/068770
§ 371 (c)(1),
(2) Date: Mar. 21, 2014

(87) PCT Pub. No.: WO2013/041723
PCT Pub. Date: Mar. 28, 2013

(65) Prior Publication Data
US 2014/0221521 A1 Aug. 7, 2014

(30) Foreign Application Priority Data
Sep. 22, 2011 (DE) .................... 10 2011 053 865

(51) Int. Cl.
| | |
|---|---|
| C08G 77/24 | (2006.01) |
| C07F 7/18 | (2006.01) |
| C08F 130/08 | (2006.01) |
| C08G 77/388 | (2006.01) |
| C08G 77/392 | (2006.01) |

(52) U.S. Cl.
CPC ............ *C07F 7/1892* (2013.01); *C08F 130/08* (2013.01); *C08G 77/388* (2013.01); *C08G 77/392* (2013.01)

(58) Field of Classification Search
CPC ... C07F 7/1892; C08F 130/08; C08G 77/388; C08G 77/392
USPC ............................................. 528/32, 30, 38
See application file for complete search history.

(56) References Cited

U.S. PATENT DOCUMENTS

| | | | | |
|---|---|---|---|---|
| 3,627,806 | A | * | 12/1971 | LeGrow .................... 556/427 |
| 4,429,082 | A | | 1/1984 | Lee et al. |
| 4,652,610 | A | | 3/1987 | Dowbenko et al. |
| 4,652,664 | A | * | 3/1987 | Singer et al. ............... 556/427 |
| 4,687,709 | A | | 8/1987 | Brinkmeyer et al. |
| 4,720,534 | A | * | 1/1988 | Singer et al. ................. 528/28 |
| 4,777,233 | A | * | 10/1988 | Suzuki et al. ................ 528/32 |
| 5,091,440 | A | * | 2/1992 | Griswold .................... 522/99 |
| 5,233,006 | A | * | 8/1993 | Wolter et al. ................ 528/32 |
| 5,412,133 | A | * | 5/1995 | Eckberg .................... 556/427 |
| 5,532,398 | A | * | 7/1996 | Wolter et al. ............... 556/420 |
| 5,919,885 | A | * | 7/1999 | Wolter et al. ................ 528/32 |
| 6,124,491 | A | | 9/2000 | Wolter et al. |

(Continued)

FOREIGN PATENT DOCUMENTS

| | | |
|---|---|---|
| DE | 10349766 A1 | 6/2005 |
| DE | 102008059129 A1 | 5/2010 |

OTHER PUBLICATIONS

T. E. Müller et al.: "Hydroamination: Direct Addition of Amines to Alkenes and Alkynes", Chem. Rev. 2008, 108, 3795-3892.

*Primary Examiner* — Margaret Moore
(74) *Attorney, Agent, or Firm* — Duane Morris LLP

(57) ABSTRACT

The present invention relates to a process for a chain extension of radicals bonded to silicon via carbon in silanes or siloxanes while maintaining or increasing the number of functional groups on the respective Si—C-bonded radicals, wherein a silane or siloxane with a radical bonded to a silicon atom by a carbon atom, which bears at least two functional groups, wherein a first group of the functional groups is an unsaturated, organically polymerizable group and a second group of the functional groups is selected from among (a) additional unsaturated, organically polymerizable groups,
(b) $COOR^8$ or $—(O)_bP(O)(R^5)_2$ and (c) —OH, with $R^8$ equal to $R^4$ or $M_{1/x}^{x+}$ wherein $M^{x+}$ is a hydrogen or an x-fold positively charged metal cation, and b=0 or 1,
is converted in a first reaction with a compound of a formula (I)

$$X—W—(Z)_a \qquad (I)$$

wherein
X is SH, $NH_2$ or $NHR^4$, Z is OH, the carboxylic acid radical —COOH or a salt or an ester of this radical or a silyl radical, W is a substituted or non-substituted hydrocarbon, the chain of which can be interrupted by —S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, and a is 1, 2, 3, 4 or a greater whole number,
wherein $R^4$ is a non-substituted or substituted hydrocarbon radical,
$R^5$ is a non-substituted or substituted hydrocarbon radical or $OR^6$,
$R^6$ is hydrogen or a non-substituted or substituted hydrocarbon radical to such an extent that the radical X connects to the first functional group.

19 Claims, No Drawings

(56) References Cited

U.S. PATENT DOCUMENTS

| | | |
|---|---|---|
| 6,794,527 B1 | 9/2004 | Wolter et al. |
| 7,977,404 B2 * | 7/2011 | Wolter et al. ................. 523/116 |
| 2008/0187499 A1 | 8/2008 | Wolter et al. |
| 2009/0023883 A1 | 1/2009 | Wolter |
| 2010/0184880 A1 | 7/2010 | Fukui |
| 2011/0082250 A1 | 4/2011 | Wolter |
| 2014/0088279 A1 | 3/2014 | Wolter et al. |

* cited by examiner

HYDROLYSABLE AND POLYMERIZABLE SILANES WITH ADJUSTABLE SPATIAL DISTRIBUTION OF THE FUNCTIONAL GROUPS, AND USE THEREOF

The present invention relates to a process for a chain extension of radicals bonded to silicon via carbon in silanes or siloxanes. These radicals contain at least two functional groups, and it is the objective of this invention to push at least one of these two groups "further outward" in a molecule through extension of the chain located between it and a silicon atom, wherein this group should either be maintained or replaced by another functional group. In one specific embodiment of the invention, additional functional groups should be introduced into the process pursuant to the invention. If individual steps of the process are repeated through the introduction of additional functional groups, dendrimer-like structures can be achieved as a result.

In the area of dental materials, though not exclusively there, it is essential to be able to provide a range of materials that can be used for the same purposes and have the same physical and mechanical properties, wherein, however, these properties must be adapted to specific, and frequently even individual requirements to the smallest detail. Examples are the color or translucence of crowns, matrix hydrophily, contraction, and reactivity to substrates or further matrix or composite elements, such as dental tissue, co-reactants or reactants in ionomer composites. In this case, minimal changes frequently have a great effect. If the specialist, for example a dentist or an orthodontist, working with these materials, can resort to a structured range of materials necessary for his own purposes, he will be able to select the appropriate material for each individual application.

In the last 20 years, a variety of silanes have been developed, which are not only hydrolytically condensable, but can also be subjected to an organic polymerization, for example, via reactive double bonds. Through polymerization of existing double bonds as well as the reaction of potentially existing additional reactive groups, a multitude of condensates, polymers, and composites can be produced from or with these silanes, which are suitable for a variety of applications. Examples of such materials are revealed in DE 40 11 044 A1, DE 44 16 857 C1, DE199 10 895 A1, DE 103 49 766 A1 und DE 101 32 654 A1. However, the various functional groups in the silanes are still relatively close to each other in these materials as well as close to the molecular nucleus.

The purpose of the invention is to create a remedy and to provide processes, with which these functional groups, which are bonded to silicon through a carbonaceous chain and a carbon atom of this chain, can be moved to a position that has a greater distance to the respective silicon atom. Due to the structural arrangement of this chain in the silicic acid polycondensates that can be obtained from silanes (which can also be referred to as siloxanes or "ORMOCER®e"), such movements may cause an extreme effect. In some embodiments, it is preferable that the originally available functional group is replaced with another functional group.

It may also be preferred to bond additional functional groups to the silicon-bonded radical throughout the course of such movements. Additional groups, such as hydroxy groups or acid groups, can positively influence the matrix hydrophily or other properties of the condensates, polymers, and composites produced from the silanes. Furthermore, this allows for the simultaneous formation of a dendrimer-like structure on a carbonaceous radical upon repeated execution of the extension reactions.

In solving the given problem, the present invention is based on structures of a following formula (1)

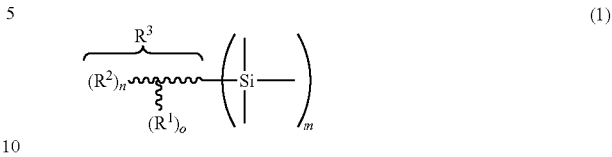

In this formula, the zigzag line represents a backbone of a hydrocarbon radical bonded to the silicon by a carbon atom, wherein this backbone can be interrupted at will by heteroatoms or linkage groups or other groups containing heteroatoms. Examples are interruptions by —S—, —O—, —NH—, —C(O)O—, —NHCH(O)—, —C(O)NH— and the like. Due to the fact that the structure of the backbone of this radical is not essential for the purpose of the invention, the specialist may make a random selection in this case.

The entire radical bonded to the silicon atom by a carbon atom is designated with $R^3$ in formula (1). It can bear additional, potentially basically likewise reactive substituents, which, however, do not then play a role for the present invention. $R^1$ refers to an unsaturated, organically polymerizable radical. In this context, the attribute "polymerizable" or the respective noun "polymerization" refer to a polyreaction, for which reactive double bonds transform into polymers under the influence of heat, light, ionized radiation or redox-induced (e.g. with an initiator (peroxide or the like) and an activator (amine or the like)) (addition polymerization or chain-growth polymerization). In this process, neither a separation of molecular components occurs nor a migration or rearrangement. Thus, examples for $R^1$ are radicals with one or more non-aromatic C=C double bonds, preferably double bonds accessible to a Michael addition, such as styryls or (meth)acrylic acid derivatives. The radical $R^1$ normally contains at least two, preferably up to approx. 50, though potentially even more carbon atoms. In the process, an organically polymerizable group can be bonded directly to a carbon network of a hydrocarbon radical or via a linkage group. Preferably, the organically polymerizable radical has at least one C=C double bond, and more preferably it is accessible to a Michael addition. In specific embodiments, it is or has at least one acrylate or methacrylate group.

The expression "(meth)acrylic . . . " presently means that, in each case, it can be dealing with the respective acrylic or the respective methacrylic compound or a mixture of both. The present (meth)acrylic acid derivatives comprise the acids themselves, potentially in an activated form—esters, amides, thioesters, and the like.

The radical $R^2$ can have the same meaning as $R^1$. Alternatively, $R^2$ can be a hydroxy group, a phosphorous radical, for example, a phosphorous acid, a free carboxylic acid or an ester or a salt of these acids.

If a structure (1) represents a silane, the three bonds of the Si atom not further identified stand for additional radicals bonded to a silicon atom. Instead, they can symbolize oxygen bridges to additional silicon atoms or other metal atoms if said structure (1) is a component of a silicic acid (hetero) polycondensates. (The expression "(hetero) polycondensates" means that the condensate, in addition to silicon, may have other metal atoms of co-condensed compounds, for example, B, Al, Ti, Zn, and/or additional transition metal atoms). Due to the fact that the reactions relevant to the invention can occur on monomeric silanes as well as on inorganically linked silicic acid polycondensates, the nature this bond is not essential. In the case of monomeric silanes, these radicals, for instance under hydrolysis conditions, can be hydrolysable groups, as they are referred to by specialists, for example, halogenides or alkoxides. Instead, one or more of these groups can represent OH. In other embodiments, at least one radical of the bond symbolizes at least one additional radical bonded to the silicon atom by carbon, which can have any number of properties. They can deviate from those of radical $R^3$; alternatively one or even two such radicals can have the meaning of $R^3$.

The indices m and n stand independently from each other for 1 or 2, though potentially for 3, 4 or even greater. Frequently, m and n are respectively 1, wherein, however, in some cases n may mean 2, 3, or even 4. Theoretically, there is no upward limitation.

The index o is highly variable and, in the case of silicic acid condensates, does not have to represent a whole number. It should preferably be at least 0.2 and is frequently between 0.5 and 1.0. However, it can also be greater than 1, e.g. 1.5 or 2.0, or even higher. If the index o is not a whole number, i.e. not every radical $R^3$ in the polycondensate has one (or more) radicals $R^1$, said radicals $R^3$, which are free from $R^1$ or do not have the maximum number thereof, instead generally have those substituents, from which $R^1$ was previously formed. This can likewise be reactive, although it does not play any further role then in the scope of the invention (see e.g. the second example of the first reaction shown further below).

The branching of the hydrocarbon backbone depicted in formula (1) shown with the diverging zigzag line is optional. In specific embodiments, radical $R^1$ can namely be a substituent, which is directly bonded to an atom of the backbone of $R^3$. One example is the case, wherein $R^1$ represents group CHR'=CH—C(O), which is bonded directly to a nitrogen atom (N*) from the backbone of the Si—C bonded radical (symbolized by both bonds on the nitrogen pointing to the right) in the form of a (meth)acrylic acid amide (CHR'=CH—C(O)—N*=). In this case, $R^1$ can mean, e.g. hydrogen or $CH_3$.

Examples of structures capable of being used pursuant to an invention (1) are:

Silanes of a General Formula (A):

$$\{X_aR_bSi[R'(A)_c]_{(4-a-b)}\}_xB \qquad (A)$$

wherein the radicals have the following meaning:
X: hydroxy, alkoxy, acyloxy, alkylcarbonyl, alkoxycarbonyl or —NR''$_2$;
R: alkyl, alkenyl, aryl, alkylaryl or arylalkyl;
R': alkylene, arylene or alkylenarylene;
R'': hydrogen, alkyl or aryl;
A: O, S, PR'', POR'' or NHC(O)O;
B: straight-chain or branched out organic radical that is derived from a compound with at least three C=C double bonds and 5 to 50 carbon atoms;
a: 1, 2 or 3;
b: 0, 1 or 2;
c: 0 or 1;
x: whole number, the maximum value of which corresponds to the number of double bonds in is the compound B minus 1,
as well as silicic acid polycondensates derived thereof formed by hydrolytic condensation of the silanes of formula (A). Such silanes and polycondensates are revealed in DE 40 11 044 A1. They fall under present structural formula (1) with $R^1$ and $R^2$ equal to an organically polymerizable radical.

Silanes of a General Formula (B):

$$B\{A\text{-}(Z)_d\text{-}R^1(R^2)\text{—}R'\text{—}SiX_aR_b\}_c \qquad (B)$$

wherein the radicals and indices have the following meaning:
A=O, S, NH or C(O)O;
B=straight-chain or branched out organic radical that is derived from a compound with at least one C=C double bond and 4 to 50 carbon atoms;
R=alkyl, alkenyl, aryl, alkylaryl or arylalkyl;
R'=alkylene, arylene, arylenalkylene or alkylenarylene with respectively 0 to 10 carbon atoms, wherein these radicals can be interrupted by oxygen and sulfur atoms or by amino groups;
$R^1$=nitrogen, alkylene, arylene or alkylenarylene with respectively 1 to 10 carbon atoms, wherein these radicals can be interrupted by oxygen or sulfur atoms or by amino groups;
$R^2$=OH or COOH;
X=hydroxy, alkoxy, acyloxy, alkylcarbonyl, alkoxycarbonyl or —NR''$_2$;
R''=alkyl or aryl;
Z=CO or CHR, with R equal to H, alkyl, aryl or alkylaryl;
a=1, 2 or 3;
b=0, 1 or 2;
as well as silicic acid polycondensates derived thereof and formed by hydrolytic condensation of the silanes with formula (B). Such silanes and silicic acid polycondensates are revealed in DE 44 16 857 C1. They represent the structures of formula (1), wherein $R^2$ is a hydroxy group or a carboxylic acid group.

Silanes of a General Formula (C)

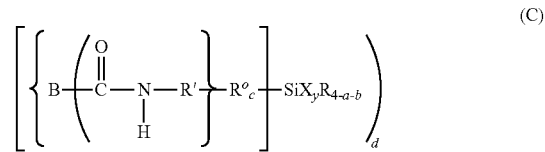

wherein the radicals and indices have the following meaning:
B=organic radical with at least one C=C double bond;
R=alkyl, alkenyl, aryl, alkylaryl or arylalkyl;
$R^o$ and R' respectively=alkylene, alkenylene, arylene, alkylenarylene or arylenalkylene;
X=hydroxy, alkoxy, acyloxy, alkylcarbonyl, alkoxycarbonyl or —NR''$_2$ with R'' equal to hydrogen, alkyl or aryl;
a=1, 2 or 3
b=1, 2 or 3, with a+b=2, 3 or 4;
c=1;
d=1, 2, 3, 4, 5, 6, 7, 8, 9 or 10;
e=2 or 3 or 4;
as well as silicic acid polycondensates derived thereof and formed by hydrolytic condensation of the silanes of formula (C). Said silanes of formula (C) and the silicic acid polycondensates capable of being derived thereof are revealed in DE 199 10 895 A1. They fall under the structures of formula (1), in which $R^2$ is an organically polymerizable radical. In the case that b represents 2 or 3 in formula (C), one or two of the additional bonds of the silicon atom have the meaning of $R^3$ in formula (1)

Silanes of a General Formula (D):

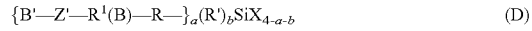

$$\{B'\text{—}Z'\text{—}R^1(B)\text{—}R\text{—}\}_a(R')_bSiX_{4-a-b} \qquad (D)$$

wherein the radicals and indices have the following meaning:
R is an alkylene, arylene or alkylenarylene group, which can be interrupted by one or more oxygen or sulfur atoms or carboxyl or amino groups, or can carry such atoms/groups on its end facing away from the silicon atom;

R¹ is an alkylene, arylene or alkylenarylene group substituted by Z', which can be interrupted by one or more oxygen or sulfur atoms or carboxyl or amino groups, or can carry such atoms/groups on one of its ends;

R¹ is an alkyl, alkenyl, aryl, alkylaryl or arylalkyl group;

B and B' can be equal or different; both radicals have the meaning of a straight-chain or branched organic group with at least one C=C double bond and at least two carbon atoms;

X is a group, which can enter a hydrolytic condensation reaction through the formation of Si—O—Si bridges (with the exception of hydrogen and halogen);

Z' have the meaning —NH—C(O)O—, —NH—C(O)— or —CO(O)—, wherein both of the initially mentioned radicals are bonded to radical B' by an NH group, while a carboxylate group can point in both directions;

a represents 1 or 2 and b is 0 or 1;

as well as silicic acid polycondensates derived thereof, which can be obtained by hydrolytic condensation of the silanes (D). Such silanes and polycondensates are revealed in DE 103 49 766 A1; they can be subsumed under structure (1), wherein R² is an organically polymerizable radical.

Silanes of a General Formula (E):

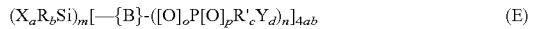

(X$_a$R$_b$Si)$_m$[—{B}-([O]$_o$P[O]$_p$R'$_c$Y$_d$)$_n$]$_{4ab}$   (E)

in which the groups, radicals, and indices have the following meaning:

B is at least a double-bonded, straight-chain or branched group with at least one organically polymerizable radical and at least 3 carbon atoms, X is a radical or OH capable of being hydrolyzed off a silicon atom (with the exception of hydrogen and halogen), R and R' are alkyl, alkenyl, aryl, alkylaryl or arylalkyl independent of each other and potentially substituted, Y is OH or OR', a is 0, 1, 2 or 3, b is 0, 1 or 2, wherein a+b together equals 1, 2 or 3, c is 0, 1 or 2, d is 0, 1 or 2, c+d together equal 2, m is at least 1 with the stipulation that m is not greater than 1 if a+b represents 1 or 2, n is at least 1, o is 0 or, and p is 0 or 1, as well as silicic acid polycondensates derived thereof, which can be obtained by hydrolytic condensation of the silanes with formula (E). Silanes of formula (E) and silicic acid polycondensates derived thereof are revealed in DE 101 32 654 A1. They fall under structure (A), wherein R² is a phosphorous radical, for example a phosphorous acid.

Silane of a General Formula (F):

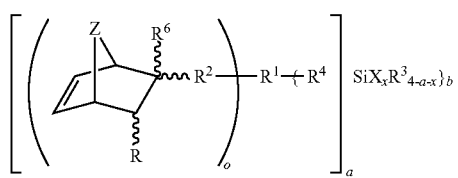

(F)

Wherein the radicals and indices are equal or different and have the following meaning:

R is hydrogen, R²—R¹—R⁴—SiX$_x$R³$_{3-x}$, carboxyl, alkyl, alkenyl, aryl, alkylaryl or arylalkyl, R¹ and R² are alkylene, arylene, arylenalkylene or arylenalkylene Independent of each other, R³ is alkyl, alkenyl, aryl, alkylaryl or arylalkyl, R⁴ is —(CHR⁶—CHR⁶)$_n$— with n=0 or 1, CHR⁶—CHR⁶—S—R⁵—, —C(O)—S—R⁵—, CHR⁶—CHR⁶—NR⁶—R⁵, —Y—C(S)—NH—R⁵, —S—R⁵, —Y—C(O)—NH—R⁵—, —C(O)—O—R⁵—, —Y—CO—C₂H₃(COOH)—R⁵—, —Y—CO—C₂H₃(OH)—R⁵— or —C(O)—NR⁶—R⁵, R⁵ is alkylene, arylene, arylenalkylene or arylenalkylene, R⁶ is hydrogen, alkyl or aryl with 1 to 10 carbon atoms, R⁹ is hydrogen, alkyl, alkenyl, aryl, alkylaryl or arylalkyl, X is hydroxy, alkoxy, acyloxy, alkylcarbonyl or alkoxycarbonyl;

Y is —O—, —S— or NR⁶,

Z is —O— or —(CHR⁶)$_m$ with m equal to 1 or 2;

a is 1, 2 or 3, with b=1 for a=2 or 3 b is 1, 2 or 3, with a=1 for b=2 or 3 c is a whole number from 1 to 6, x is 1, 2 or 3 and a+x is 2, 3 or 4.

with the condition that if c=1, R⁴ must be —Y—CO—C₂H₃(COOH)—R⁵— or —Y—CO—C₂H₃(OH)—R⁵—.

For the purpose of chain extension, the silane or the silicic acid polycondensate of formula (1) is (first) reacted with a compound of a formula (I)

X—W—(Z)$_a$   (I)

wherein

X=SH, NH₂ or NHR⁴,

W is a substituted or non-substituted hydrocarbon radical, for example an alkylene, an arylene, an arylalkylene or an alkylarylene radical or is an alkenylene radical, the carbon chain of which can be interrupted by any heteroatoms or linkage groups, such as —S—, —O—, —NH—, —NR⁴—, wherein R⁴ represents the following: —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—; and Z=OH, silyl (i.e. SiX*₃, wherein, independent of each other, the radicals X* represent a hydrocarbon radical or a hydrolysable radical-most often an alkyl or alkoxy group with 1 to 6 carbon atoms), the carboxylic acid radical (—COOH) or an ester or a salt of these acids, wherein R⁴ represents a non-substituted or substituted hydrocarbon radical-frequently alkyl, aryl, arylalkyl or alkylaryl—and is preferably an alkyl radical being more preferred with one to six carbon atoms.

With this reaction, a radical X connects to the compound (I) at the double bond of the unsaturated, organically polymerizable group R¹ and, thus, extends the structure (1) via the is linkage group A=S—, —NH— or —NR⁴ by the component W:

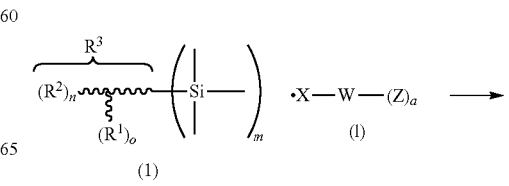

(1)

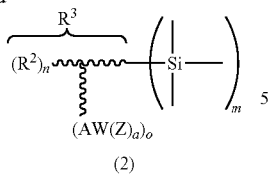

In the process, a radical Z, if working randomly, is introduced a-fold to the o-fold available Si—C-bonded radical.

The index a is 1 in many embodiments of this reaction; in specific embodiments explained in further detail below, it represents 2 or 3 or 4 or greater than 4, wherein 2 and 3 are preferred.

With this reaction, as with all reactions described in the following, it is beneficial if the compound is used with the formula (I) in a molar deficit with regard to radical $R^1$, defined as 1-α mol of the compound (I) in relation per mol of the unsaturated, organically polymerizable group $R^1$. In this context, α is preferably at least 0.05, preferably at least 0.10, in other cases at least 0.30, sometimes even at least 0.40, and in individual cases >0.50, wherein a can then even assume values of, i.e. 0.90.

This technical teaching is based on the fact that when using the compound (I) in a deficit, this compound is entirely consumed so that in the materials, for which the product of this reaction is processed, problematic monomers, potentially from a toxicological or allergological perspective, are no longer present. Moreover, it proved to be irrelevant that the radical identified with $R^1$ had to be completely converted, as a more or less large share of non-extended Si—C-bonded radicals in the mixture has no negative impact on the properties of the latter. And finally, a decisive benefit arises for further possible reactions—the product of the reaction does not have to be cleaned or processed in any way and can therefore be immediately and easily subjected to a subsequent reaction as is preferred for the present invention.

In one preferred embodiment of this reaction, X represents SH in the compound of formula (I). In this variation, a radical —W—Z of the compound of formula (I) is bonded to the unsaturated, organically polymerizable group of the radical bonded to the silicon atom via a thiol-ene addition. Alternatively, X can also be $NH_2$ or, in another alternative, $NHR^4$, wherein $R^4$ has the above meaning. These radicals also connect to the unsaturated C=C double bond of the organically polymerizable group, such that the radical —W—Z is bonded by NH— or the $NR^4$ bridge to the radical that is bonded to the silicon atom.

In one preferred embodiment independent thereof, which can be combined with each of the previously mentioned embodiments, a radical Z in the compound with formula (I) represents OH or COOH. The meaning, Z=OH, is particularly preferred even, and especially, in combination with a=2 or 3, preferably a=2. If a is greater than 1, multiple groups OH (or COOH) can be further converted in a subsequent reaction explained in more detail in the following, which may ultimately result in a dendrimer-like structure.

In one preferred embodiment independent thereof, which can be combined with each of the previously mentioned embodiments, the second functional group $R^2$ of the radical bonded to the silicon is a hydroxy group or an additional unsaturated, organically polymerizable group. In the case of the latter, it can be identical with the (first) unsaturated, organically polymerizable group; however, it can also differ from this. For instance, one of the two groups can be a methacrylate group, while the other group is an acrylate group. Both of these groups have a different reactivity to radical X from the compound of formula (I) so that, in such case, a selective course of reaction occurs, while, in the other case, an unspecific mixture arises. The latter is less preferred.

The reaction of the silane or silicic acid polycondensate with structure (1) with the compound of formula (I) is designated as the "initial reaction" within the context of the present compound. This will be explained in further detail in the following based on a variety of examples.

As an output material, a silicic acid polycondensate is used in the first of these examples as structure (1), which was produced through hydrolysis and condensation of a silane of general formula (B) (preferably in the "Sol-Gel" process):

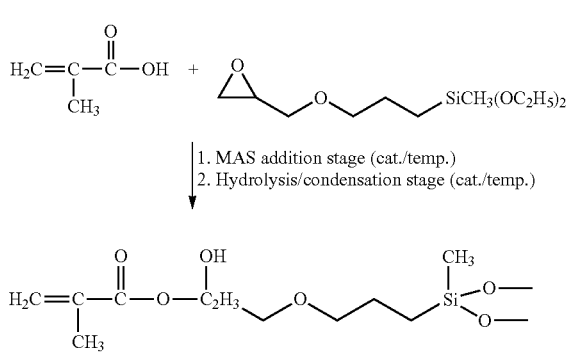

This structure, which is designated as "Base Resin I" in the following, is then reacted with a compound of formula (I), X being a mercapto group, Z being a hydroxy group, W being a saturated hydrocarbon group with three carbon atoms, and a=2:

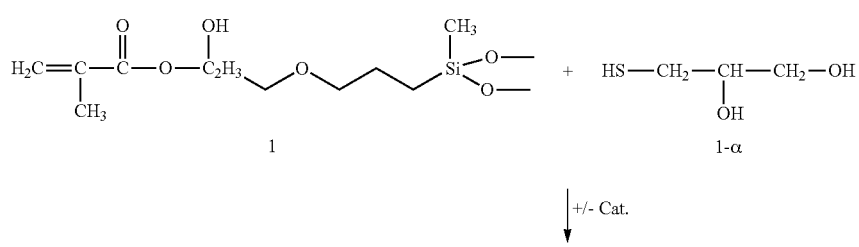

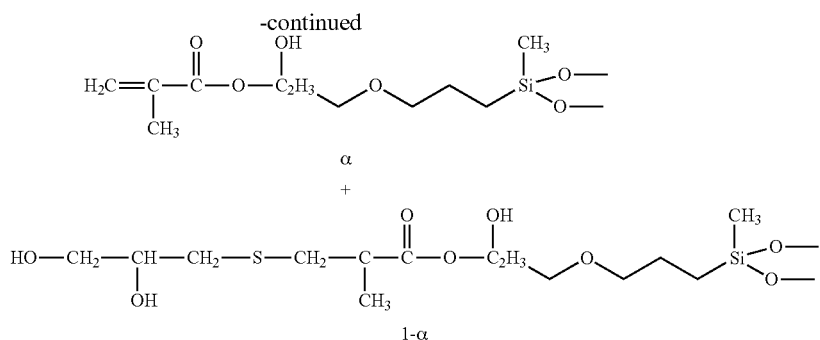

The product of this reaction (application examples 1a and 1b) contains a radical $R^3$ extended by one sulfur atom and three carbon atoms, in which the original functional group (the organically polymerizable group) is replaced by a hydroxy group. Furthermore, the product contains an additional hydroxy group. It contains one thioether group as a linkage group A.

Instead of a compound with formula (I), in which X is a mercapto group, this reaction could also be conducted with a compound of formula (I), in which X is a primary or, less preferred, a secondary amino group. With regard to the chain extension highlighted by the invention, the selection of radical X does not play a role, as it is only responsible for the structure of linkage group A between the newly linked radical —W—Z and the radical molecule, which—with a single exception—has no technical function or effect. This exception involves the mercapto group, the use of which as radical X offers a specific benefit—the integration of the sulfur atom as a linkage group A in the makeup of the Si—C bonded radical causes an increase of the refractive index $n_D$ of the formed silicic acid polycondensate compared to a secondary or tertiary amino group.

Instead of a diol used in the example for the compound of formula (I), mono-alcohols may naturally be used as well; in this case, the additional introduction of hydroxy groups is omitted. Alternatively, compounds with more than two hydroxy groups may also be used as a compound of formula (I).

In another variation of the invention, a compound of formula (I) is used for the initial reaction, in which the radical Z represents a silyl group or a carboxylic acid radical ($CO_2H$) or an ester or a metallic salt of said carboxylic acid radical. Even mixed compounds are possible, i.e. those compounds that have a hydroxy as well as an acidic function.

Specific examples for compounds of formula (I) are:

Thiols functionalized with OH having only one hydroxy group, such as:
  6-Mercapto-1-hexanol,
  4-(Mercaptohexyloxy)-benzyl alcohol,
  2- or 3- or 4-Mercaptophenol,
  11-Mercapto-1-undecanol,
  1-Mercaptoundec-11-yl)-tetraethylene glycol.
Thiols functionalized with $CO_2H$:
  11-Mercaptoundecanoic acid
  3-Mercaptopropionic acid
  3- or 4-Mercaptophenyl acetic acid
  16-Mercaptohexadecanoic acid
  6-Mercaptonicotinic acid
  8-Mercaptooctanoic acid
  15-Mercaptopentadecanoic acid
  4-Mercaptophenyl acetic acid
  Mercaptosuccinic acid
Thiols functionalized with a silyl radical:
  3-Mercaptopropyltrimethoxysilane,
  3-Mercaptopropyltriethoxysilane,
  3-Mercaptopropylmethyldimethoxysilane.

If Z in compound (I) is a silyl radical, groups are introduced, which permit an additional inorganic hydrolysis and condensation.

A silicic acid polycondensate serves as an output material in a second example of the initial reaction, which was produced through hydrolytic condensation of a silane of general formula (D):

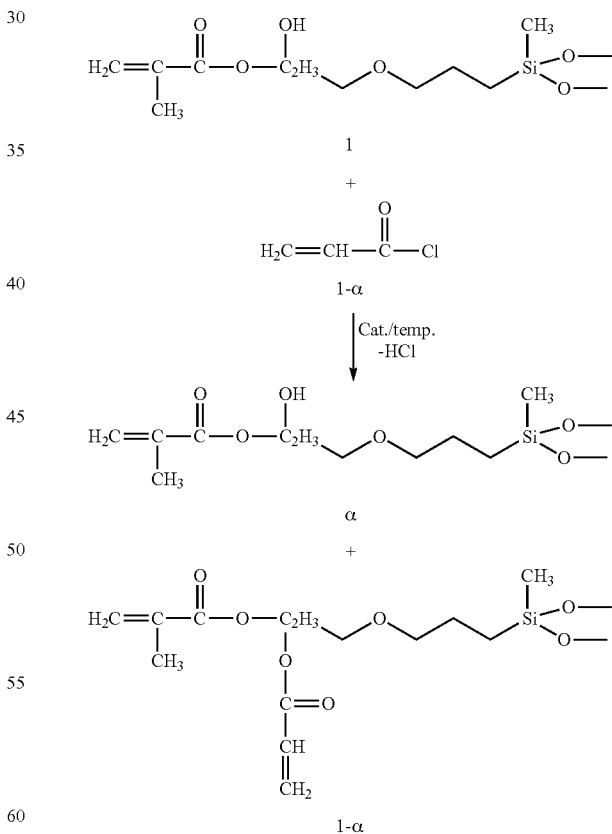

This structure is designated as "Base Resin II" in the following. Noteworthy here is that this polycondensate contains two different structures of formula (1), in which in one case $R^1$ represents an unsaturated, organically polymerizable group and OH in another, as the underlying reaction was conducted with a deficit of acrylic acid chloride. Mixed output materials of this type can be used as needed just as incompletely reacted (i.e. those with o<1) present in all variations. In this regard, a ratio is potentially preferably used of 0.6 to 0.95 mol of the reagent introducing radical $R^1$, e.g. 0.6 to 0.95 mol of acrylic acid chloride per mol of hydroxy group for the introduction of an acrylate group is used as $R^1$; instead of this, however, the acrylic acid compound can naturally also be used as needed up to molar equivalence or, in some case, even beyond. However, the latter is frequently unbeneficial with respect to the desire to prevent the presence of monomer radicals in a resin.

The structure with formula (D) is then converted with a compound of formula (I) in this second example as well, X being a mercapto group, Z being a hydroxy group, W being a saturated hydrocarbon group with three carbon atoms, and a=2:

the reaction is stereospecific—the acrylate radical is extended. Due to the addition of thiol, we can observe a drastic increase of polarity/hydrophily as a result of the increase of the OH content and—surprisingly—an extremely high deflection to the point of breakage after the hardening, while the breaking strength and the modulus of elasticity are decreased (see also Example 5a).

With regard to the possible variation of this exemplary reaction through the use of other compounds of formula (I) Instead of 3-Mercaptopropan-1,2-diol, it is necessary to refer to the entire explanation for the first example. Naturally, all specified compound types or specific examples for compound (I), which were mentioned for the first reaction in conjunction with the explanation for the first example, can be used for this reaction in combination with the second example.

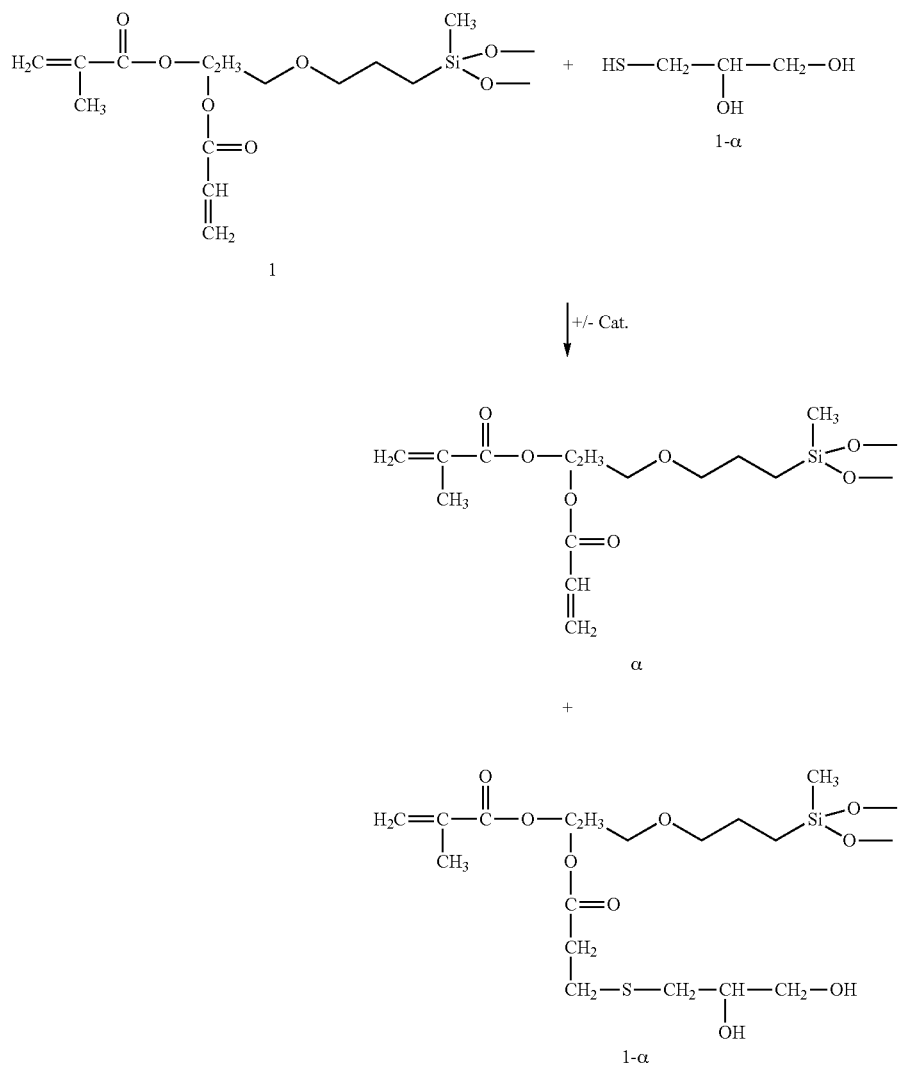

In this example, both $R^1$ and $R^2$ are each unsaturated, organically polymerizable groups; however, they differ from each other. The reaction with compound (I) has been selected in the process in such a manner that SH is preferably added to the acrylate group and not to the methacrylate group. Thus, As an example for a compound (I), in which X is an amino group, the reaction of the structure with formula (D), as it was previously demonstrated for the second example, is represented with a hydroxy-substituted, secondary amine (third example of the first reaction):

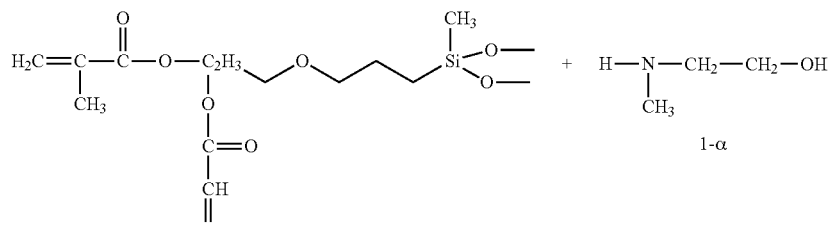

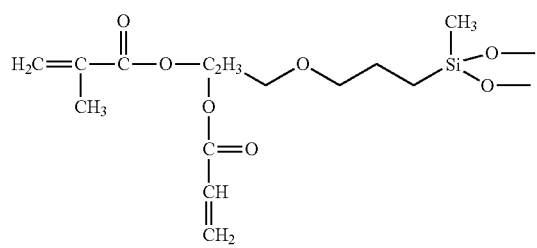

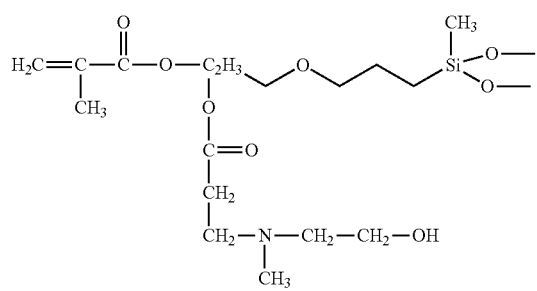

The difference to the previous example is only in the type of linkage group (in this case a tertiary amine instead of a thioether bridge), which, as explained above, is functionally inessential (although the refractive index can be varied by the provisioning or omission of the thioether group), the use of a molecule that is shorter by one $CH_2$ group and by the presence of only one hydroxy group (a=1) (see also application example 7a).

Even with this reaction, a cannot only represent 1, but rather 2 instead (or potentially 3 or 4 or more), as the following example shows:

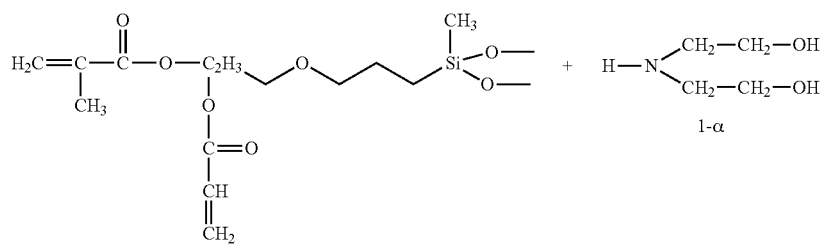

-continued

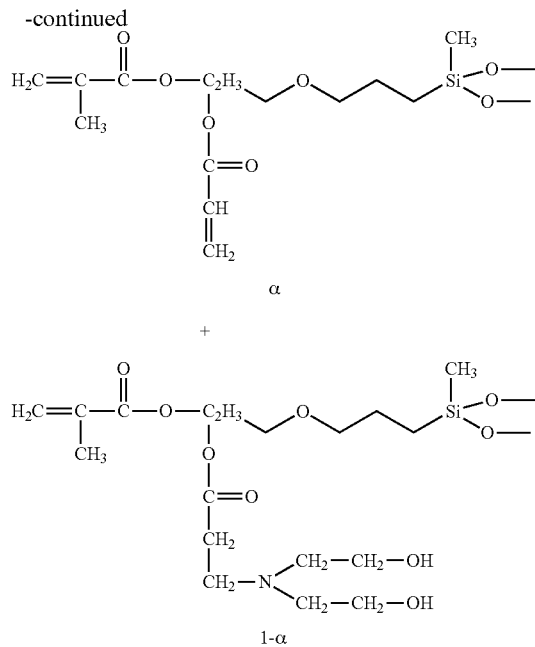

(The reaction above is specifically described in Application example 9a). The polarity/hydrophily can be adjusted, e.g. through the OH content of the amine compound. This can be freely selected over a broad range among primary and secondary amino groups with one, two or even more hydroxy or other groups Z as defined above.

The initial reaction does not necessarily have to occur to already hydrolytically condensed silanes, as previously shown. Instead, it can naturally be conducted to monomeric silanes.

The final product of the first reaction can, for example, have an unsaturated, organically polymerizable group as well as one or two, potentially even more, hydroxy groups. Instead of hydroxy groups, carboxylic acid radicals —COOH, carboxylic acid salts or carboxylic acid ester may naturally be present as well if said compound (I) is used with respective groups Z.

The functional groups introduced in the first reaction may principally be used for varying purposes:

(1) The introduction of one or more acid groups leads to an improvement of the bonding and/or etching properties of the achieved silicic acid polycondensate or the respective polymer or composite.

(2) The functional groups introduced by the first reaction (particularly OH groups) can serve the variation of the polarity and/or hydrophily.

(3) Additional compounds can be linked to the Si—C-bonded radical. Thus, on one hand, a respective functional group can again be shifted further outward; on the other, the originally present unsaturated, organically polymerizable group can be reproduced through this type of reaction, which is then likewise located in a position further out. Lastly, the group shifted outward in this manner can then again be randomly converted, e.g. in the case of a hydroxy group with phosphorous pentoxide or phosphoryl chloride with the formation of a phosphoric acid ester. Thus, we obtain a new bonding group that is located far out.

The product (2) of the first reaction can be the final product of the invention; the benefits of this product are listed in the following section under (1) and (2).

If a compound of the formula (I) was used for the first reaction, wherein Z represents a hydroxy or a carboxylic acid group or a salt or ester of the carboxylic acid radical, i.e. it is not a silyl radical, or if an Si—C-bonded radical $R^3$ was used for the first reaction, in which $R^2$ represents an OH group, the products (2) of the first reaction can be further converted in a second reaction pursuant to the invention. This second reaction may occur according to three different variations. This is explained in further detail in the following:

First Variation of the Second Reaction:

In the first variation, the silane or the silicic acid polycondensate with the structure (2), wherein Z=OH or COOH, is converted with the compound of the formula (II):

(II), wherein Y is NCO, an epoxy or—only for the event that Z is a hydroxy group —COA', wherein W is defined as in compound (I), $R^1$ is an unsaturated, organically polymerizable group as defined in conjunction with formula (I), A' represents hydroxy, a halogenide or —OC(O)$R^4$ with $R^4$ equal to a non-substituted or substituted hydrocarbon, e.g. alkyl or alkylene, k=0 or 1, wherein k=0 is only possible in the event that Y represents COA', and b=1 or is greater than 1, for example, 2, 3 or 4. In other words, the compound or condensate with the structure (2) is converted with an isocyanate, a compound containing an epoxy group or an (activated) carboxylic acid. As a result, an additional radical —W—$(R^1)_b$ is bonded to the Si—C-bonded radical of the silane or silicic acid polycondensate via a linkage group B, which is an ester, ether, acid amide or urethane group depending on whether or not Y connects to a hydroxy group or a carboxylic group:

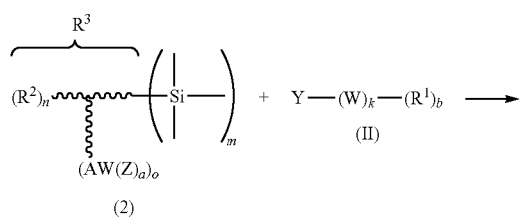

(2)

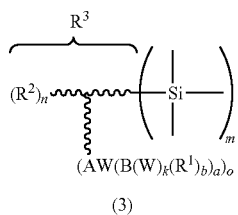

(3)

In the process, the compound (II) can carry multiple radicals $R^1$ (i.e. b can be 1, 2 or even greater), such that the number of double bonds per Si—C-bonded radical can be increased. In combination with a first reaction, for which the compound (I) carries two or even more radicals Z, a dendrimer-like structure of this type can be applied.

Thus, the product of the first variation of the second reaction is in turn a compound or a condensate with at least one radical $R^1$ and at least one radical $R^2$ on the Si—C-bonded radical $R^3$, wherein, however, the radical $R^1$ is distanced from the silicon atom with respect to radical $R^1$ in the output material, which is extended through both reactions by A-W—B—W— and is present b times a-fold with respect to the original number o in the output material. The presence of a greater number of double bonds that can move relatively well across longer chains, which are essentially located in the outer area of the silane molecule or the siloxane, can lead to a decrease of the contraction for subsequent cross-linking, which can be particularly advantageous in the dental field. Furthermore, the radical of $R^3$ can potentially have additional functionalities, e.g. through the use of a compound of formula (I), which has at least two hydroxy groups, and/or a compound of formula (II), which has more than one unsaturated, organically polymerizable radical.

The first variation of the second reaction is explained in further detail in the following on the basis of examples. The first of these two examples are based on the product of the first example above for the first reaction; the third example is based on the product of the second example above for the first reaction:

The First Example for the Second Reaction (Reaction of a Compound Containing a Hydroxy Group with one Isocyanate, in this Case, an Isocyanate (Meth)Acrylate (Variation 1)

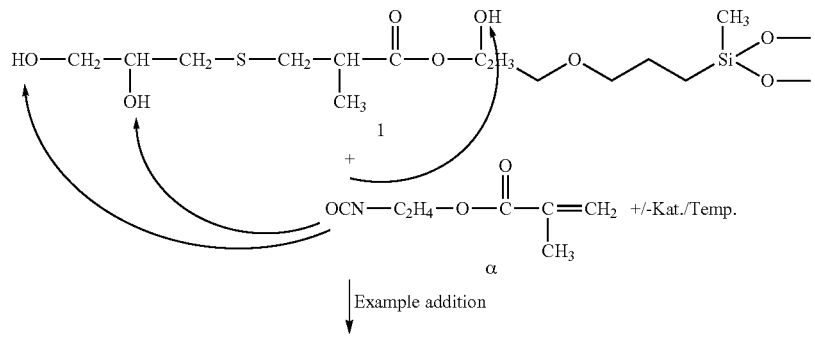

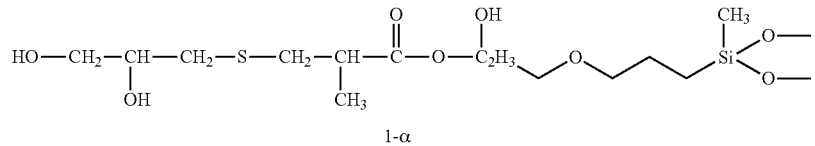

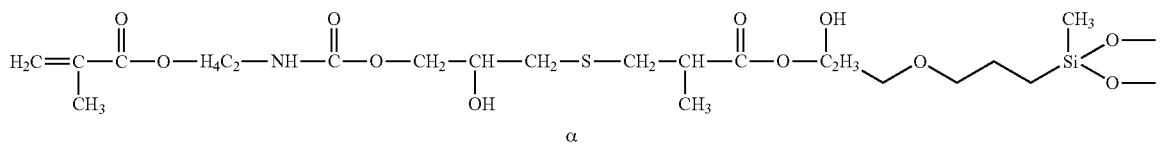

The product is identified with (3-1). The preferred, though not exclusive, point of connection of the isocyanate-methacrylate as a compound (II) is the primary hydroxy group on the Si—C-bonded radical. Thus, a mixture arises with a primarily silyl-methacrylate structure, in which the methacrylate group was shifted outward by the group $H_4C_2NH$—$C(O)$—$O$—$CH_2$—$CH(OH)$—$CH_2$—$S$ with respect to those of the output compound (1). Due to the fact that the output material for this reaction does not have to be the pure reaction product of the first reaction, but rather can be present in the mixture with unreacted material of the first reaction, a finely graded spectrum of products with strong, but varyingly improved physical properties, such as breaking strength, modulus of elasticity or deflection, can be produced, while surprisingly the hardening shrinkage does not further increase (see Application example 2b to 2e with the respective values for these parameters).

reacted secondary hydroxy group arises or an Si—C-bonded radical with three methacrylate groups.

If the reaction occurs, for example, with three mol of compound (II) (i.e. α=3 in the upper formula scheme), we obtain a product with the structure (3), wherein all three hydroxy groups are replaced by methacrylate groups. Based on a structure having one C=C double bond and one hydroxy group as the two functional groups of the output material, we will thus achieve, e.g. structures with three methacrylate groups laying far from each other, which respectively hang on the lateral chains of the Si—C-bonded radical (the reaction scheme is depicted further below; Structure 3-2) through combination of the first and second reaction.

Naturally, the first variation of the second reaction can also be conducted with compounds (II), in which b is greater than 1. One example for a reaction (II) with b=2 is shown in the following, which identifies the resulting structure with (3-3):

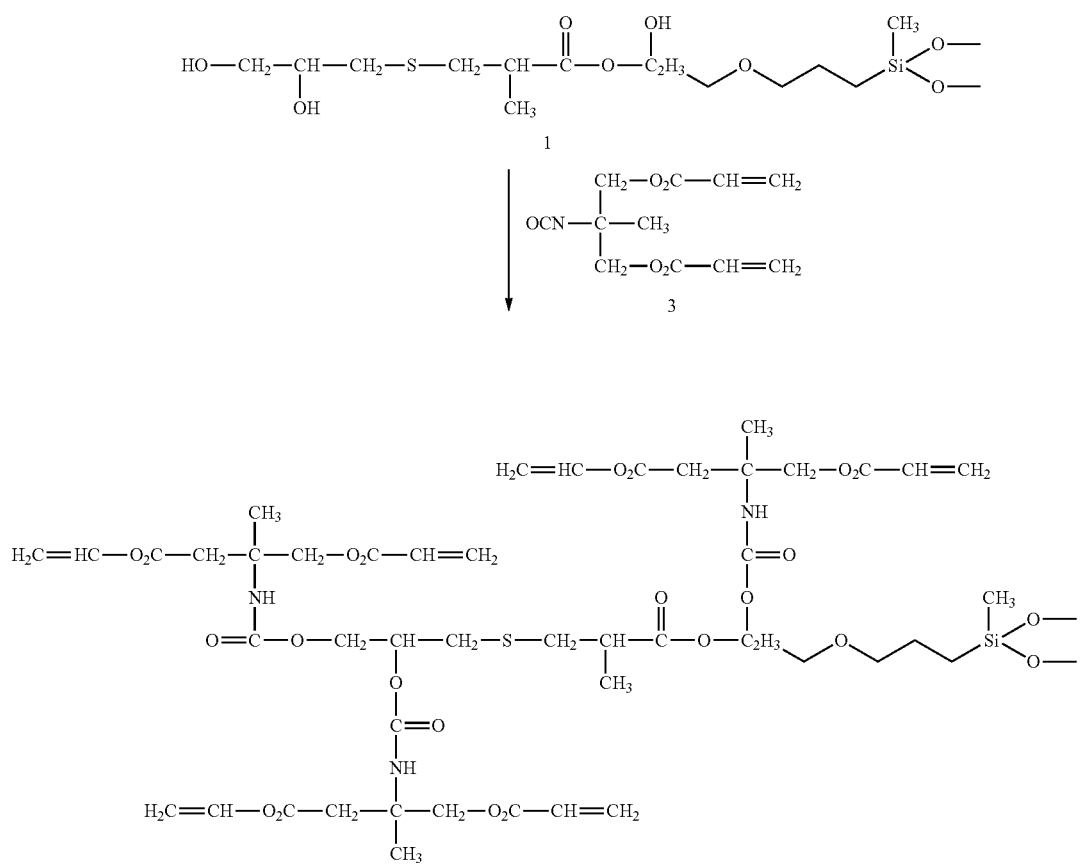

In this example on the other hand, a deficit on the compound (II) can be used so that a part of the output material remains unreacted, as was described above for the first reaction (see Example 6a). In this example, however, more than one molar equivalent (III) can also be used instead due to the fact that overall three hydroxy groups are present on the Si—C-bonded radical, which can potentially react with the isocyanate (II) as well, see Application example 6b. Depending on the amount of compound (II) used, which can be up to 3 molar equivalents, either a mixture having a partially The original radical $R^2$ is likewise converted in this structure (3-3) and therefore changed its meaning with respect to the definition in structure (1) to $B$—$(W)_k$—$(R^1)_b$. This is naturally also true for all comparable reactions—if $R^2$ in a structure (2) represents Z (equal or different than the remaining groups Z of structure (2)), this radical can generally be involved in the following reactions and for its part contribute to the outward shifting of radicals or dendrimerization.

The reactions occur analogously if a reactant carries groups containing carboxyl groups instead of hydroxy groups; this results in acid amide groups.

Second Example for the Second Reaction (Variation 1):

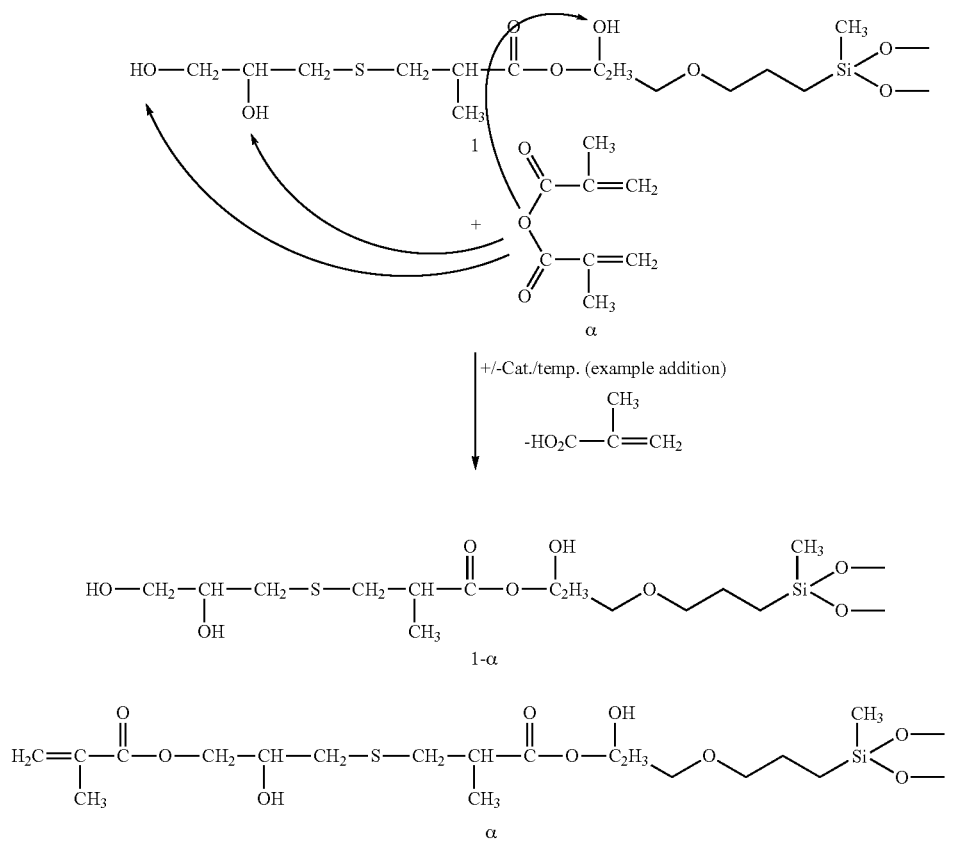

This example differs from the previous in that instead of an isocyanate, an anhydride (in this case the anhydride of methacrylic acid) is used; the product is shorter than that of the first example for this reaction by one ethyl urethane unit. The same product could be achieved with another activated methacrylic acid, e.g. with methacrylic acid chloride. In this case, an extreme increase of the strength and modulus of elasticity was able to be observed as well (see also Application example 3).

With regard to the molar ratios, the same applies respectively as described for the previous example.

Third Example for the Second Reaction (Variation 1):

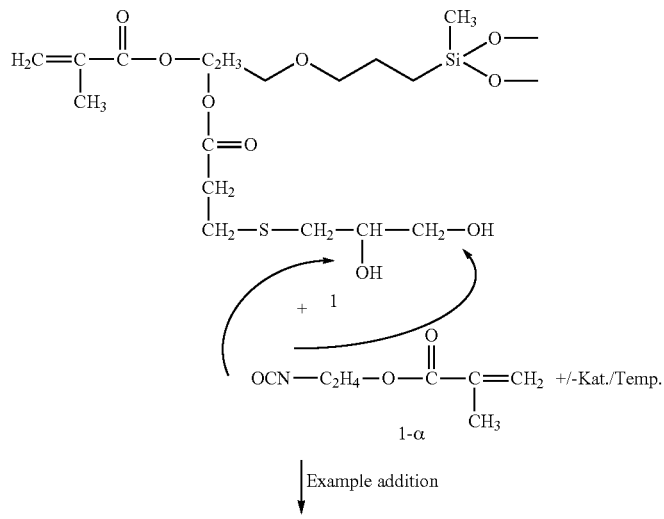

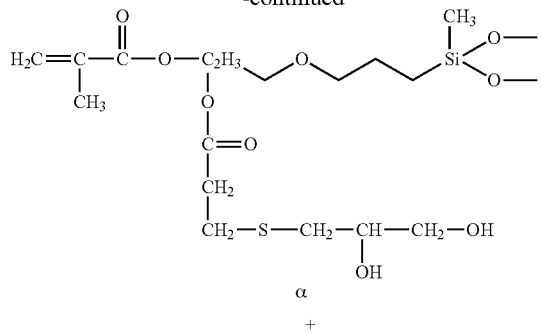

α

+

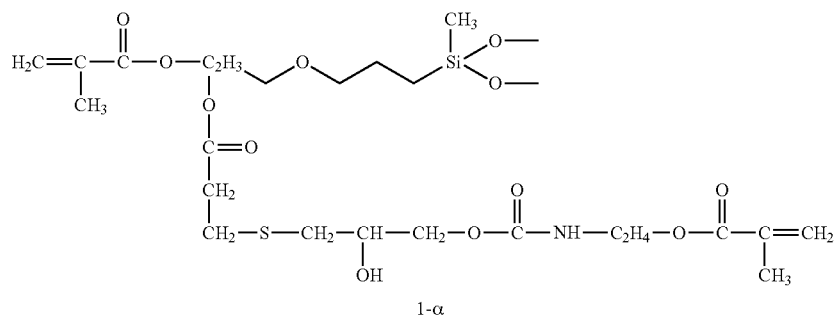

1-α

Even in this case, either (barely) a mol of isocyanate of formula (II) or up to two mol of isocyanate can be used; accordingly one product is obtained, for which the methacrylate group is clearly shifted outward compared to the output material, and that carries either a second methacrylate group or an additional hydroxy group. With respect to the latter variation, it is necessary to note the application examples 6a and 6b—the addition of an isocyanate methacrylate leads to an extreme increase of the breaking strength of the modulus of elasticity with a high degree of deflection.

Instead of a product of the first reaction, which was obtained through the reaction with a mercapto compound, for example, a product achieved with an amine may be used as output material, e.g. the above shown product of the reaction of a structure with formula (D) with a hydroxylamine, which was reacted in this case with Isocyanate methacrylate.

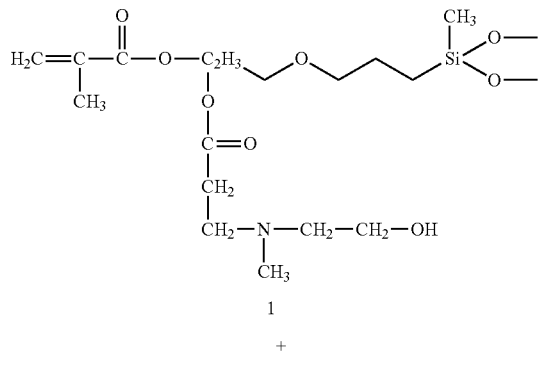

1

+

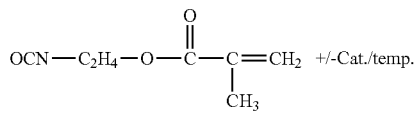

1-α

Example addition

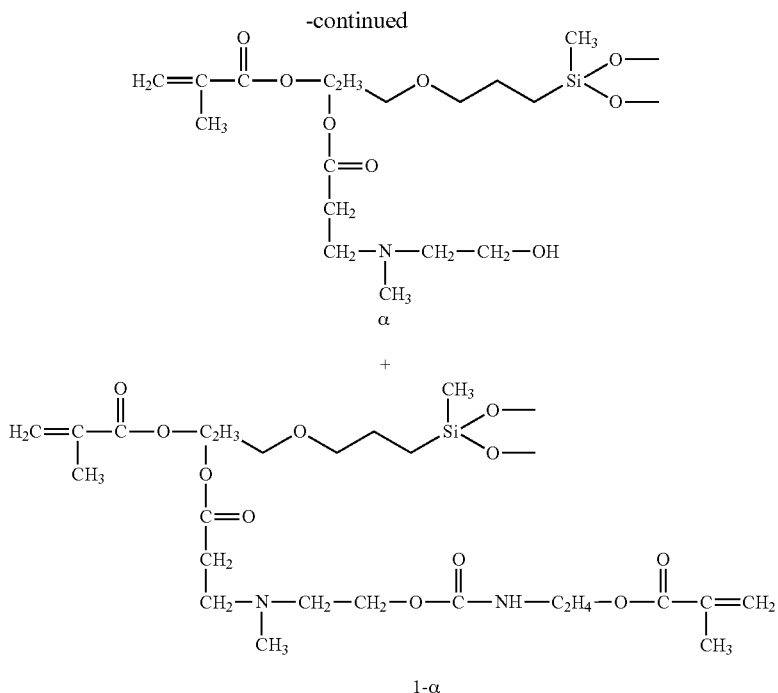

α

+

1-α

If the product with Di(2-hydroxyethyl)amine is used instead of that of the reaction of the above shown structure with formula (D), a mixture is achieved, see, e.g. Application example 10a. Depending on the amount of compound (I) or compound (II) used relative to the base resin, the properties of the product will vary—see Application example 8a to 8c.

The products (3) of the first variation of the second reaction contain double bonded organically polymerizable groups, which are arranged at a greater distance to the Si atom on the Si—C-bonded radicals compared to the output material. This is one objective of the present invention. They can continue to be used in this form.

In a further development of the invention, however, they can in turn serve as output material for an additional cycle from the first and potentially second reaction. As a result, they allow the unsaturated, organically polymerizable groups to be shifted even further outward, etc.; instead of this, products with additional reactive groups can be obtained as described above. If additional functional groups are introduced in the process, which can be likewise connected to the above described reactions, we will obtain dendrimer-like structures. Before we explain this in further detail, however, the second variation of the second reaction is depicted:

In the second variation of the second reaction, the silane or the silicic acid polycondensate with the structure (2), wherein Z=OH or COOH or a carboxylic acid salt, is converted with a compound of formula (III):

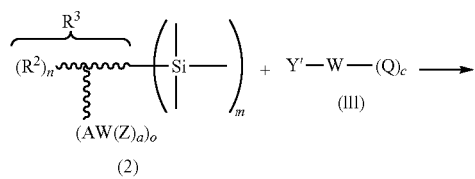

(2)

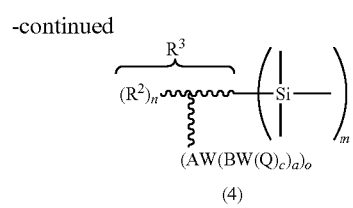

(4)

wherein Y' is defined either as Y for the compound (II) or, in the case of Z equal to COOH, an ester or a salt thereof, can instead have the meaning of $NHR^4$, $NH_2$, or OH with $R^4$ equal to a non-substituted or substituted hydrocarbon, in particular alkyl or aryl, and in the case of Z equal to OH, can have the meaning of COOH, an ester or a salt thereof, W is defined as for the compound (II) and Q is OH, $NR^7_2$, $NR^7_3{}^+$, $CO_2H$, $SO_3H$, $PO(OH)_2$ $PO(OR^4)_2$, $OPO(OH)_2$, $OPO(OR^4)_2$ or a salt of the aforementioned acids, or wherein Y' and Q together form the group —C(O)O(O)C— and W is a straight-chain, branched or cyclical alkylene or alkenylene group with preferably 2 to 12 carbon atoms or a arylene group with preferably 6 to 12 carbon atoms (thus the compound is an anhydride). c represents 1, 2, 3 or 4 or a higher whole number. $R^7$ can have the same meaning as $R^4$. In addition to this meaning, together two $R^7$ radicals can also represent a double-bonded, potentially randomly substituted, potentially unsaturated (even aromatic) hydrocarbon group; accordingly $NR^7_2$ and $NR^7_3{}^+$ can, e.g. be a pyridine radical or the radical of a cyclical ammonium compound or a pyridinium derivative or the like. Radicals Q with the meaning of $NR^7_2$ or $NR^7_3{}^+$ can have essential additional functions in a resin produced pursuant to the invention. Thus, in the case of Z, an activator molecule arises from $NR^7_2$, which can be used for a redox-hardening as discussed above. Compounds or resins with $NR^7_3{}^+$ radicals demonstrate an antimicrobial effect.

Reactions of aminosulfonic acids, such as 2-Aminoethane-sulfonic acid, are principally known and described, e.g. in the registration DE 10 2011 050 672.1 (not yet published on the filing date of the present registration).

If the radical $R^2$ is an unsaturated, organically polymerizable radical or COOH and Y' is $NHR^4$ or $NH_2$, naturally we cannot preclude in some cases, depending on the reaction conditions, that the amino group of compound (III) will connect to $R^2$ as well. In those cases, we obtain mixtures that are likewise encompassed by the invention.

A first example for the second variation of the second reaction—in this case in combination with the first reaction—is shown as follows:

(2) is produced by reacting with mercaptopropionic acid (compound of the formula (I) with X=SH, Z=—COOH and a=1), wherein the linkage group is A=S. This forms in particular when using a (maximum) of one mol of mercaptopropionic acid per mol of silane due to the fact that the addition of SH preferably passes onto the acrylate group. As a result, the formation of the above product is benefited. This product is then converted with a compound with the formula (III), wherein Y' is $NH_2$ and Q is —$P(O)(C_2H_5)_2$. A structure of a formula (4) emerges, wherein the linkage group B is an acid amide group. The group Q can be transformed into —$P(O)(OH)_2$ therein through hydrolysis.

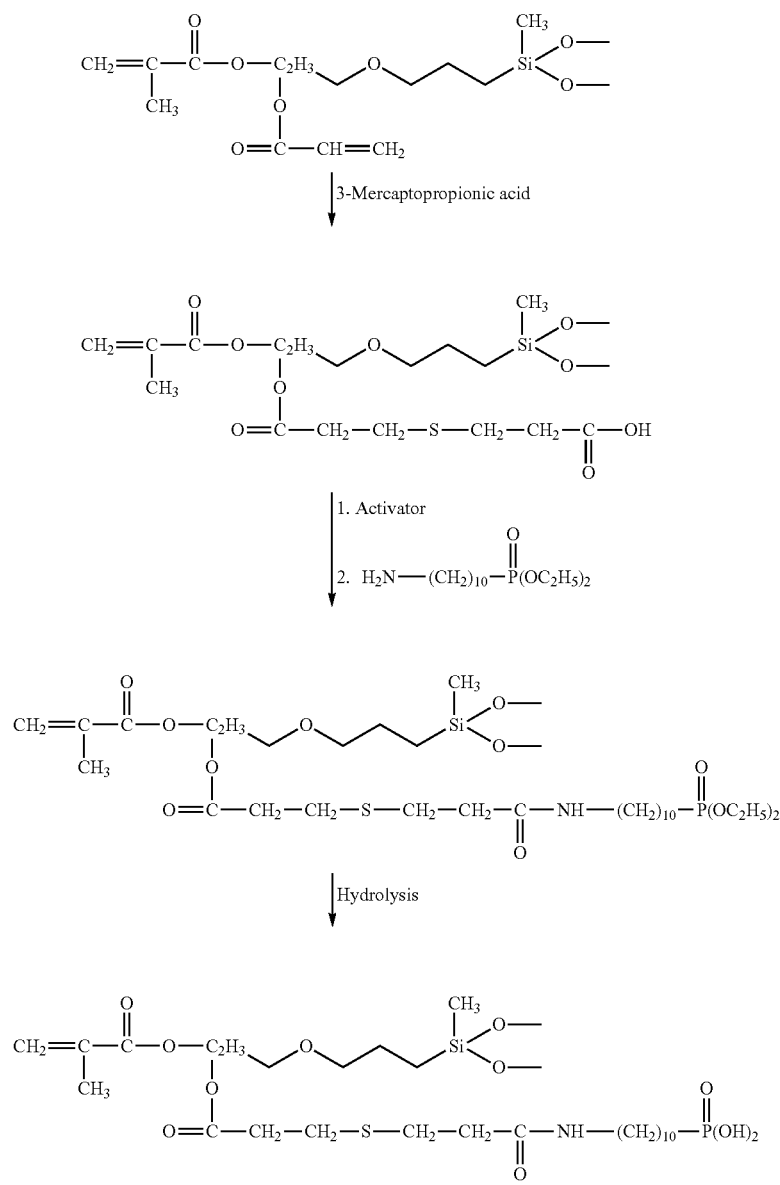

Based on a structure of formula (1), wherein $R^1$ and $R^2$ are respectively an unsaturated, organically polymerizable group, in this case an acrylate and a methacrylate group, and m and n are respectively 1, first a structure with the formula A second example for this reaction is presented based on the reaction with a compound (III), wherein Y' and Q together form the group —C(O)O(O)C— and W is an ethylene group (i.e. with succinic acid anhydride):

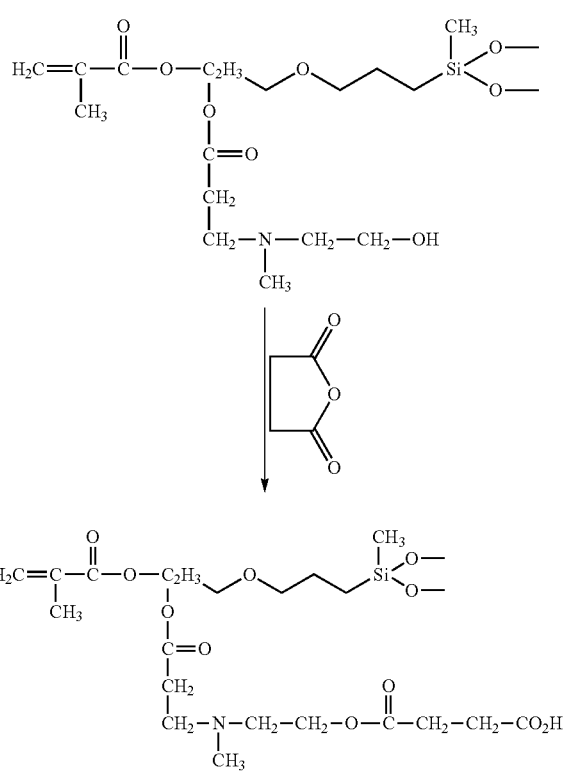

A structure of the formula (4) emerges with a linkage group $A=NR^4$ with $R^4=CH_3$ and a linkage group $B=OC(O)$ (an ester group). The extended chain carries a free carboxylic acid group on its end, which originated from the succinic acid anhydride. In the process, it is necessary to point out that this reaction cannot be depicted entirely properly with the above reaction equation $(2)+(III)\rightarrow(4)$, for Q in (III) is not identical to Q in (4) in this case.

According to the third variation of the second reaction, the product of the first reaction, wherein Z is equal to OH, is converted with phosphorus pentoxide ($P_2O_5$) or phosphoryl chloride ($POCl_3$). A product with the formula (9) emerges:

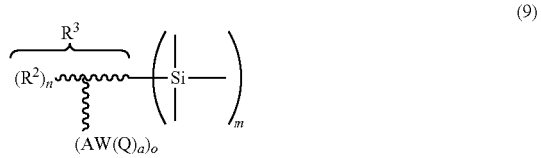

(9)

wherein Q represents —O—P(O)(OH)$_2$, while all other radicals and indices are defined as in formula (2).

The product (4) of the second variation of the second reaction can be the final product of this embodiment of the invention; with respect to the number of radicals $R^1$ in the output material, the a-fold number of reactive groups Q multiplied with c that are at a distance from the silicon atom, which is shifted outward by A-W—B—W— with respect to the original radical $R^1$, can be found therein. The product (9) of the third variation corresponds to product (4) in the event that Q represents —O—P(O)(OH)$_2$ with the modification that Q is shifted outward only by -A-W— with respect to the original radical $R^1$. The properties that arise through the connection of this functional radical were in part already explained above. Additional advantages are that in product (4), the functional groups are situated far out in the molecule relative to the silicon and, due to the long chains, can move well. This is important for possible additional effects such as the antibacterial effect or the complexation or bonding properties of, e.g. carboxylic acid, phosphorous acid or phosphoric acid groups, which have been vastly improved due to the external location of the respective groups (e.g. forming several effective "connection points").

As already explained above, the product (3), which was developed pursuant to the first variation of the second reaction, can be subjected to an additional reaction or an additional cycle of reactions. The next, namely the third reaction, can then occur in two variations:

In the first variation, the product (3) is converted analogous to the first reaction with a compound of formula (I), wherein the radicals and indices have the aforementioned meaning:

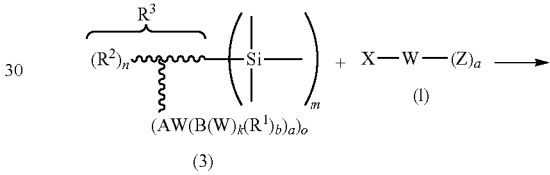

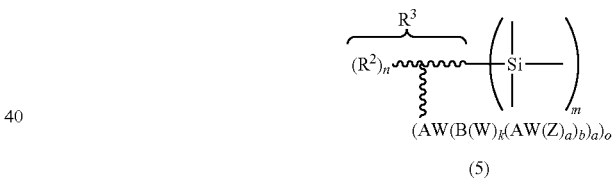

(5)

A product emerges, in which the radical Z is present several times on the Si—C-bonded radical, which corresponds to the $a^2b$-fold of o; in other words, in lieu of the originally present radical $R^1$ or each of the originally present radicals $R^1$ in the output material (1), there are a a b radicals Z in the structure (5). If, for example, a dihydroxy compound was used as a compound with the formula (I), as shown in the above examples, while a (mono)methacrylate was used as compound (II), the product (5) contains four organically polymerizable radicals containing double bonds in lieu of each original radical $R^1$ on an Si—C-bonded radical (the number of which corresponds to index c). If the compound with the formula (I) only contains one hydroxy group, it is only that type of radical. The same applies for the case that the index b in the compound (II) is greater than 1. The emergence of dendrimer-like structures is evident. The radicals Z are shifted outward beyond that with respect to the output material (1) by the group A-W—B—W-A-W.

One example for the first variation of the third reaction is shown below:

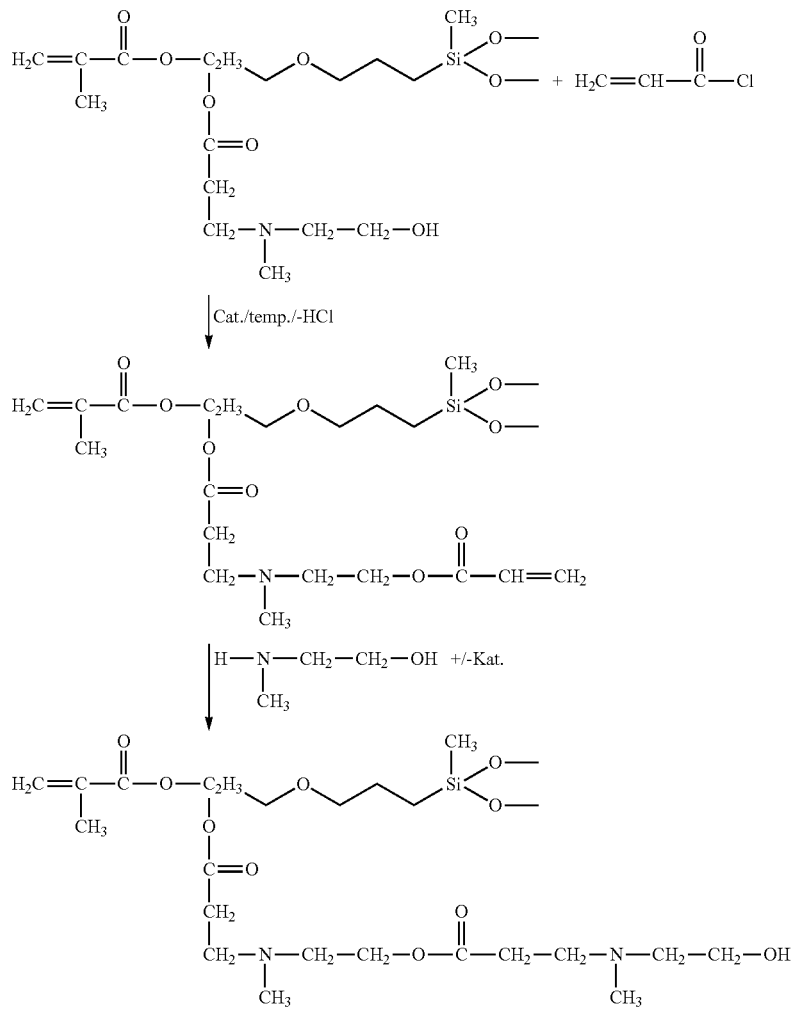

Based on the product of the above shown third example of the first reaction, a structure (3) with A=NR⁴, R⁴=CH₃, B=ester group is formed through a reaction with a compound (II), wherein Y=COA', in this case with A'=chloride, R¹=vinyl, b=1 and k=0 (a and o are likewise respectively 1 in this case). This is then converted with a compound of the formula (I), wherein X=NHR⁴ with R⁴=CH₃, Z=OH and a=1. A structure (5) emerges, in which the second linkage group A is then NR⁴ with R⁴=CH₃. The other groups, radicals, and indices arise from the above explanations to the reactions and compounds. This is identified as structure (5-1).

If we instead assume the above explained structure (3-2), which was achieved with 3 equivalents compound (II) in the second reaction through the reaction of a structure (2), which contains three hydroxy groups:

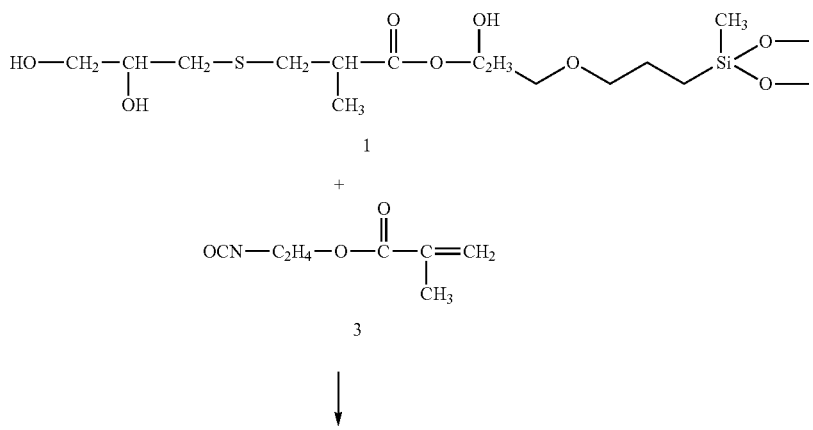

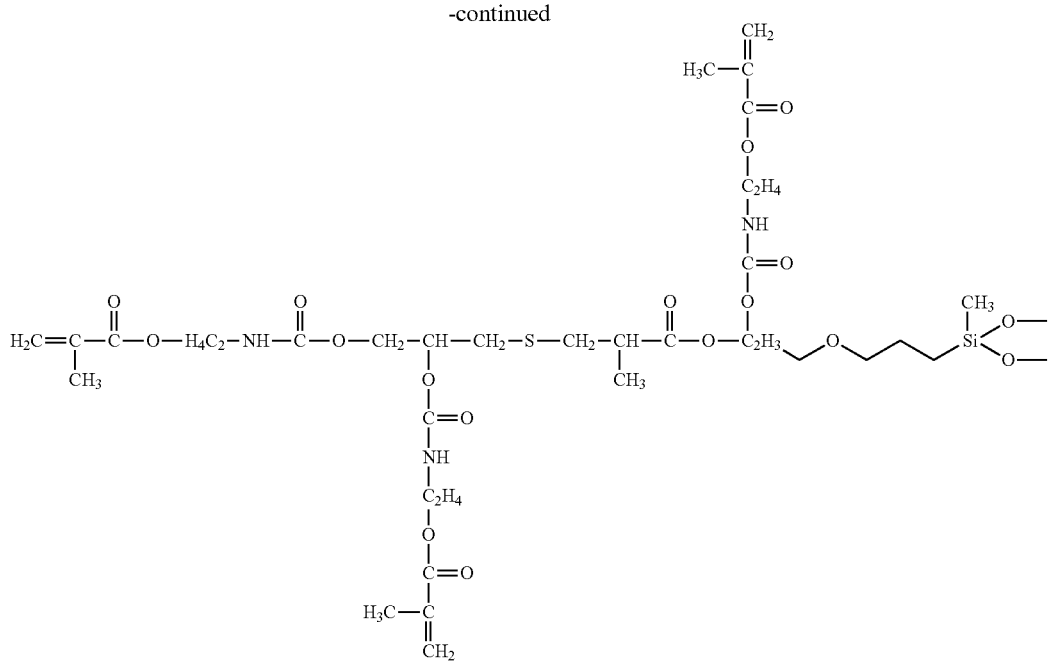

and convert them with an amount of compound (I) equimolar to the radicals $R^1$, we will obtain a dendrimer-like structure of formula (5), identified in this case as (5-2) (we see that the reactive groups Z arising in the process, namely hydroxy groups, which hang far out on three lateral chains of the Si—C-bonded radical respectively in pairs and, thus, form a dendrimer-like structure):

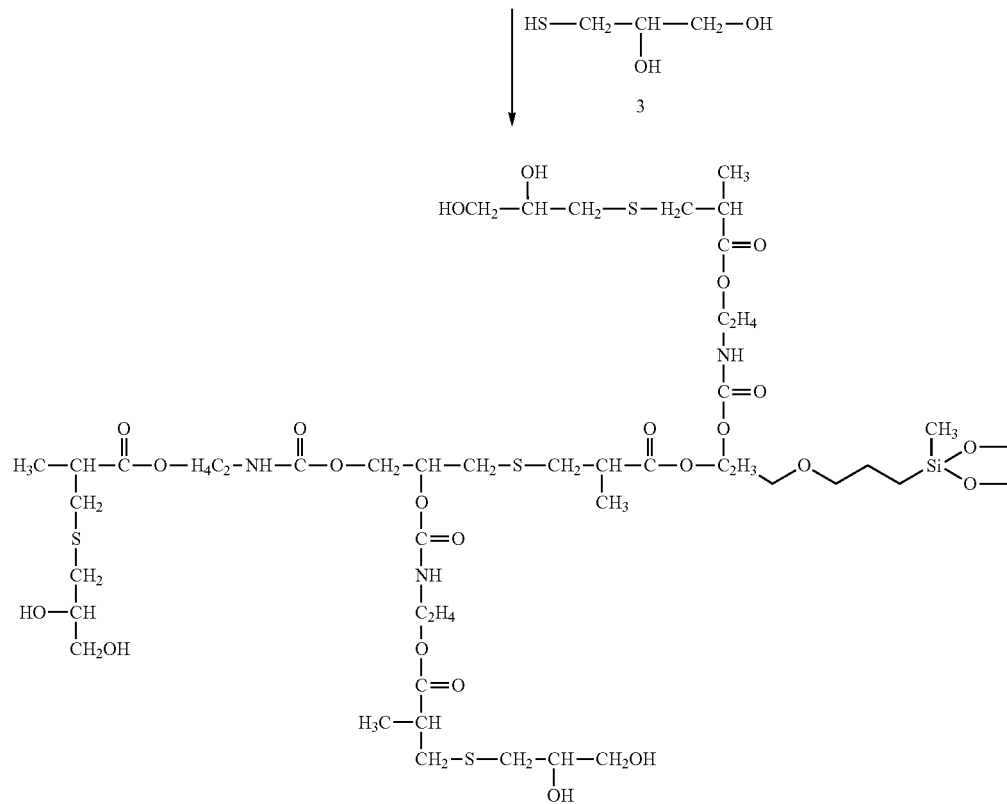

Due to the fact that in the structure (3-2), as in structure (3-3), the radical $R^2$ has likewise changed its meaning with respect to the definition in structure (1) to $B\text{—}(W)_k\text{—}(R^1)_b$, and this radical was for its part converted in the process, the former radical $R^2$ now has the meaning $B(W)_k\text{-}AW(Z)_a)_b$ in the structure (5-2).

If, instead, we assume the structure (3-3) explained above, as is described above, and convert it in a likewise equimolar manner (with regard to the $R^1$ radical) with a compound (I), in which a=2, we will obtain a product (5-3) with 12 hydroxy radicals:

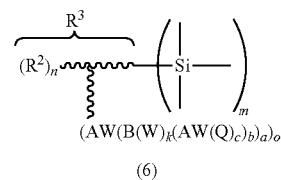

(6)

Structure (6) is comparable to structure (4), wherein, however, the number of radicals Q compared to (4) is still increased by the factor b (due to the reaction with the compound (II)) and these radicals are located one group A-W farther away from the Si atom. Accordingly, the effects are increased again with respect to those depicted for (4).

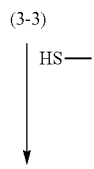

(3-3)

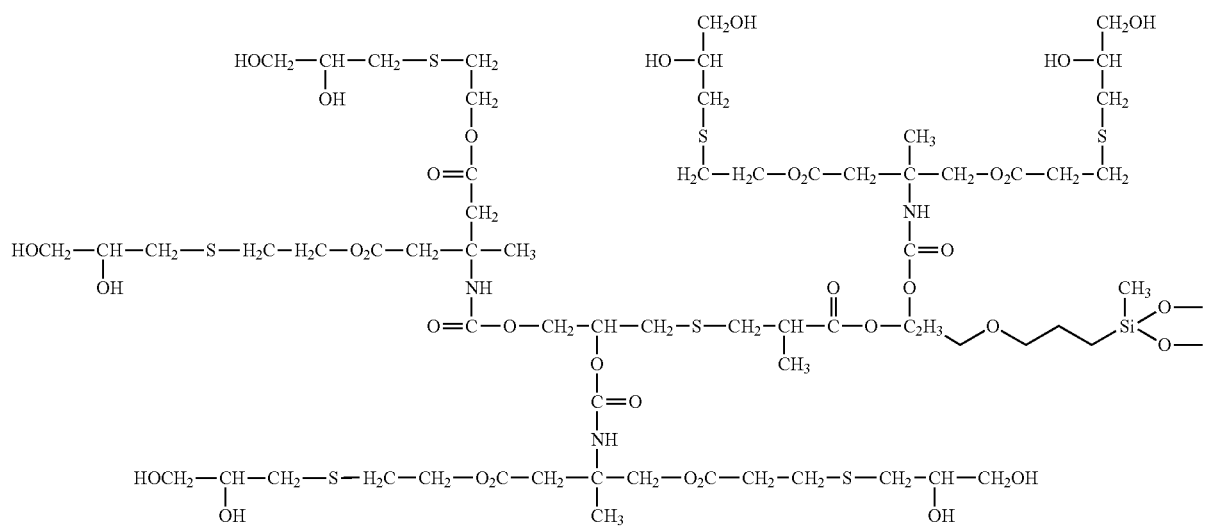

We can see that the Si—C-bonded radical branches out 6 times in (5-3), wherein two OH groups are arranged in pairs relatively close to each other on each of the branches.

In the second variation of the third reaction, the product (3) is converted in a manner similar to the second variation of the second reaction, namely with a compound of the formula (IV), wherein the radicals and indices have the meaning specified for the formulas (I) and (III):

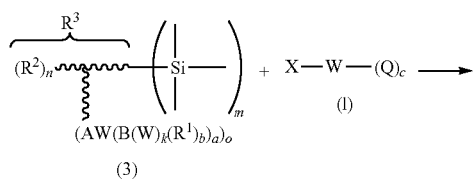

One example, which, as previously shown, is based on a structure (3) with three groups containing double bonds located far away from each other, is depicted in the following. In this example, X is an SH group in the compound (IV), Q represents a carboxylic acid group, and W represents a hydrocarbon group containing 2 C-atoms. In this formula, c represents 2:

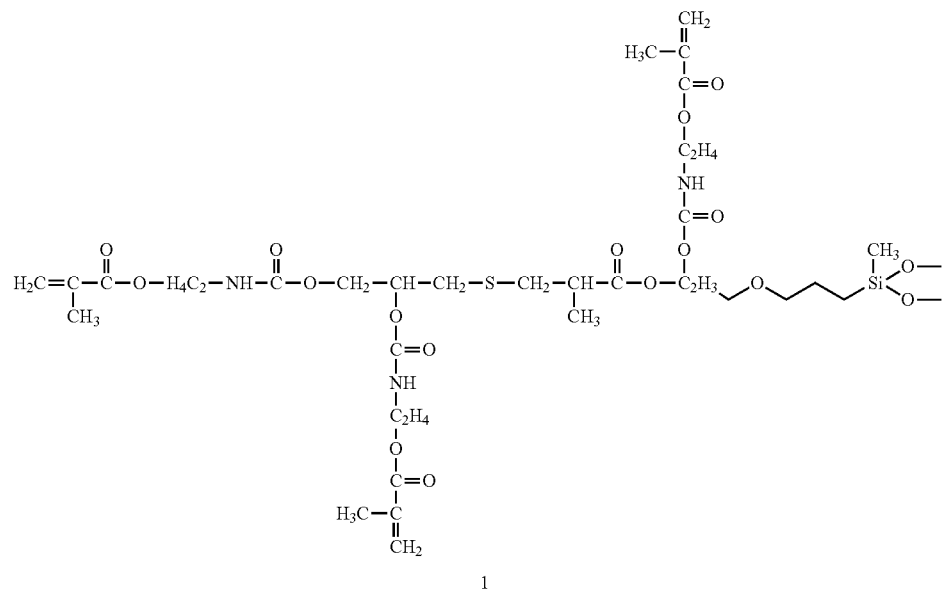
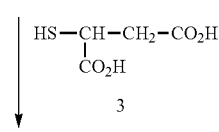
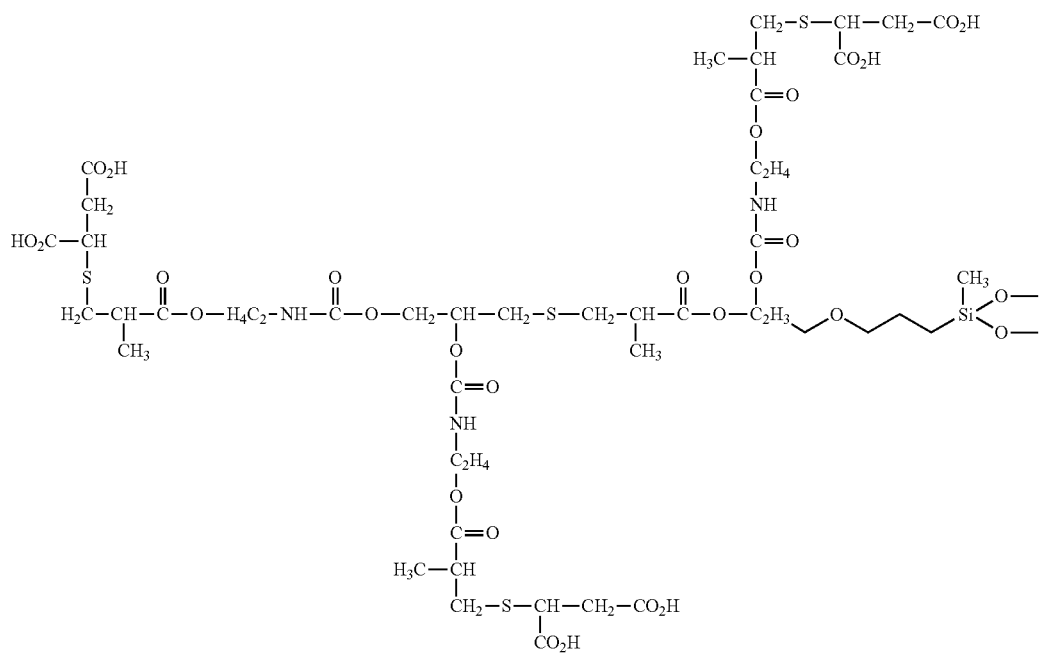

This structure (identified as 6-1) is similar to the structure (5-2) above, although in lieu of the six reactive groups Z=OH, it contains six COOH groups.

The product (5) of the first variation of the third reaction in turn can for its part be subjected to a fourth reaction in variations, namely again with a compound with the formula (II) or the formula (III). The products can be depicted as follows, wherein the radicals and indices have the aforementioned meaning:

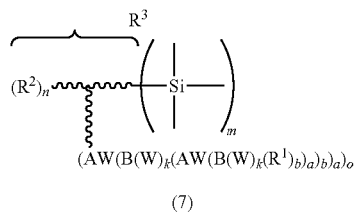

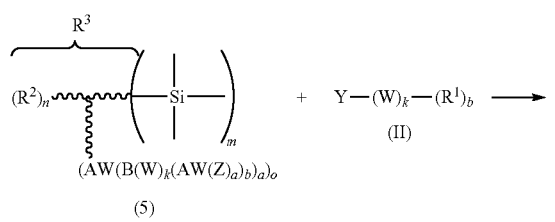

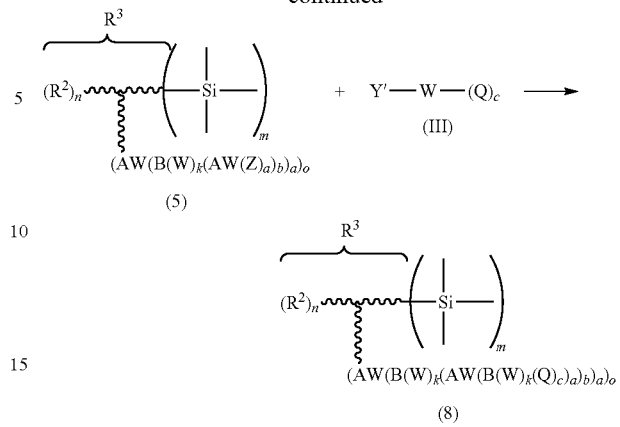

The products emerging in the process are respectively comparable with the products from both variations of the third reaction, wherein the number of radicals $R^1$, however, is present b-fold, the number of radicals Q, however, is present a-fold with respect to the products (5) and (6), namely with a once again increased distance to the Si atom. The advantages correspond accordingly to the descriptions for products (3) and (4), although they are once again increased. Accordingly, the radicals $R^2$ in (7) and (8) represent $B(W)_k(AW(B(W)_k(R^1)_b)_a)_b$ or $B(W)_k(AW(B(W)_k(Q)_c)_a)_b$.

One example for the extension of the structure (5) pursuant to the first variation of the fourth reaction with a compound of the formula (II) through the emergence of the structure (7) is shown below; it is based on the product of the first variation of the third reaction (5-1), the production of which was demonstrated with examples:

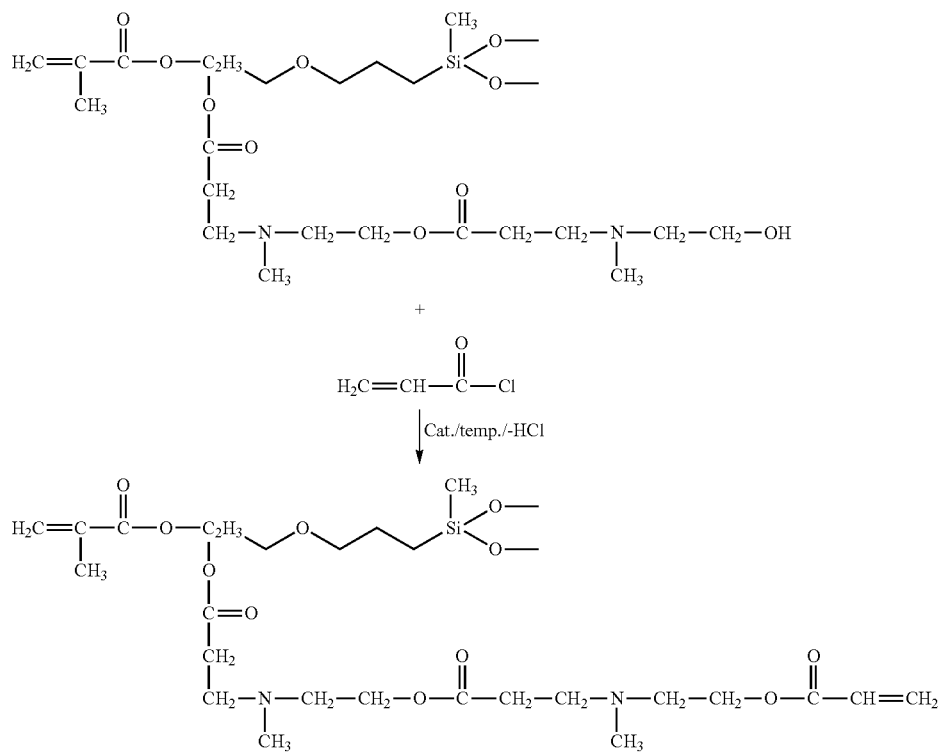

The reaction occurs in turn with a compound (II) with Y=COA' with A'=chloride, $R^1$=vinyl, b=1 and k=0. Accordingly, the product (7) contains two linkage groups A=$NR^4$ with $R^4$=$CH_3$ as well as two linkage groups B=ester group.

However, as an output material (5) if we use one with structures that contain a higher number of reactive groups Z, e.g. the above shown structure (5-2) with 6 hydroxy groups, this reaction will produce a product with a structure (7) (structure (7-1)) with a respectively high number (namely 6) of radicals $R^1$ containing double bonds, wherein the radicals containing double bonds arranged in pairs, in this case methacrylate groups, now have a significant distance to each other as well:

One example for a comparable reaction of (5) with (II) pursuant to (7) is the reaction of structure (5-3) with the following compound (II):

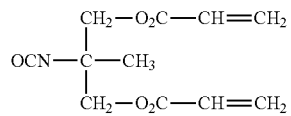

The product has the structure (7) and has 12 double bonded groups (structure (7-2)).

Based on (5-2), with the reaction with a molecule (III), we achieve a structure (8) with 6 carboxylic acid groups that are comparably arranged:

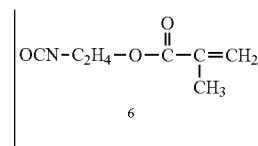

6

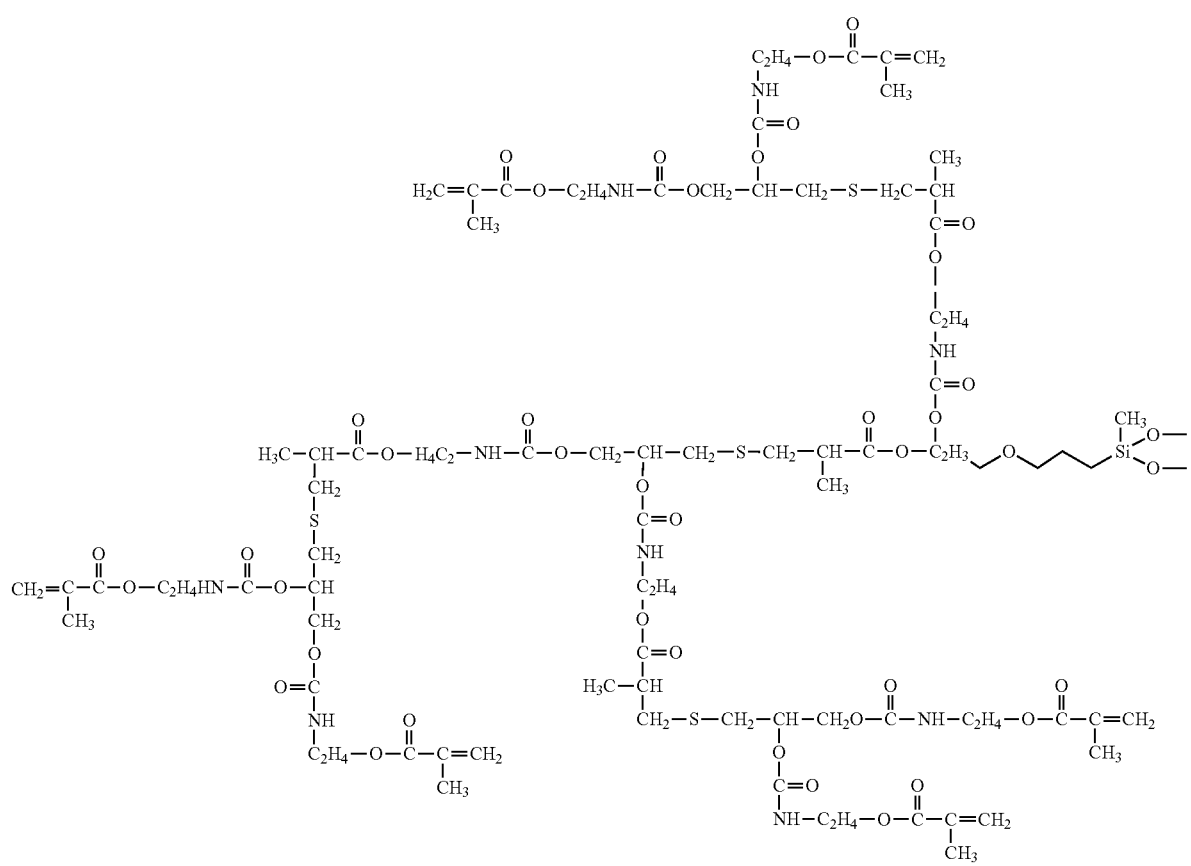

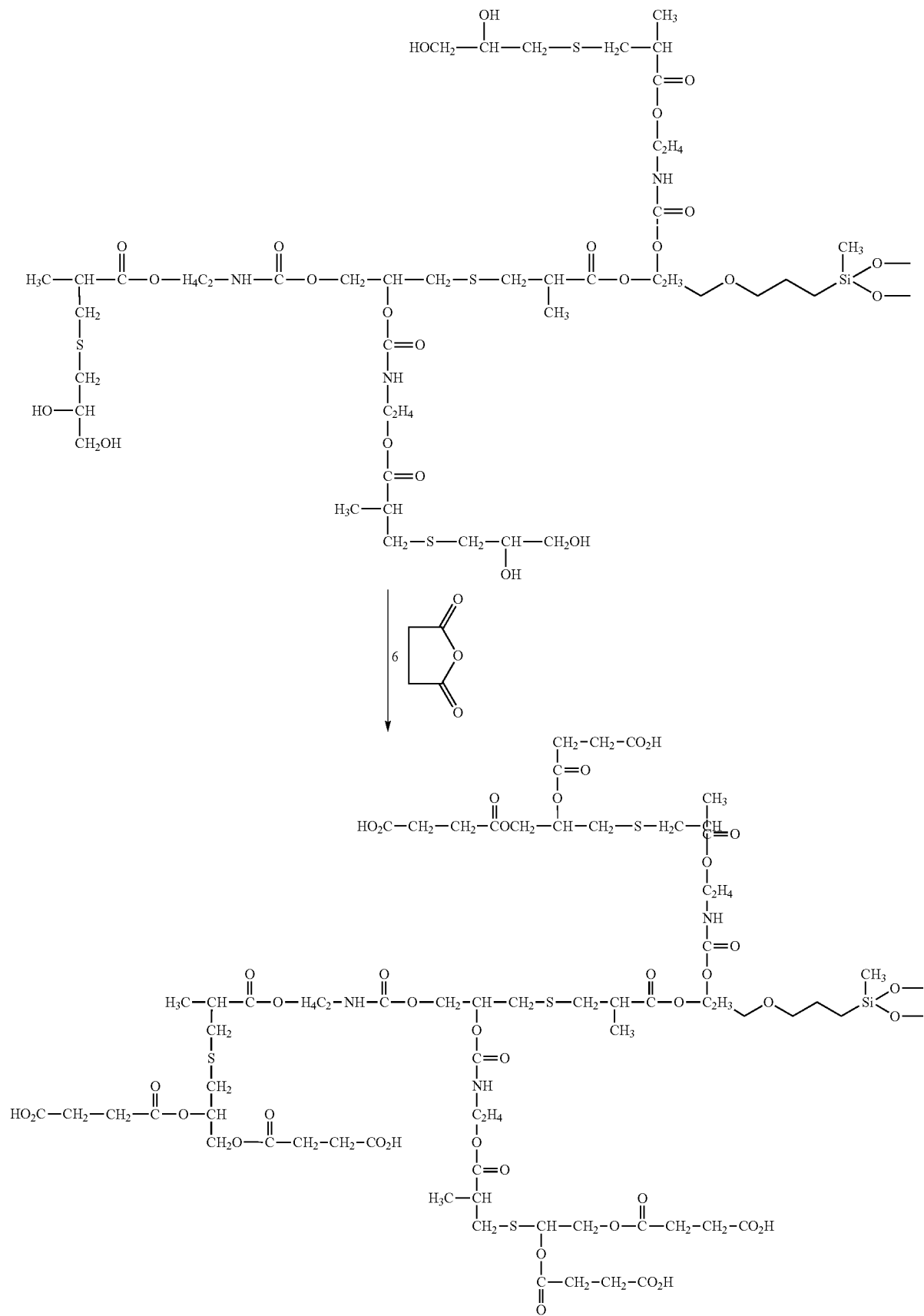

The principle of the reaction sequence can fundamentally be continued; due to the fact that the products—at least in those cases, in which X is equal to SH or Y is equal to NCO, and particularly then if the compounds (I) to (IV) are used in the deficit with regard to the respectively convertible radicals—do not have to be isolated or purified, structures with any number of reactive groups Q located far out or organically polymerizable radicals $R^1$ can be produced on respectively one Si—C-bonded radical, which are potentially branched out like a dendrimer.

If the products of a structure (3) have free, reactive groups Z, e.g. OH groups because, for instance the initial reaction occurred with compound (I), in which a >1 and the subsequent reaction of a product (2) occurred with compound (II) in the deficit, an alternative to another a reaction with a compound of formula (I) and then potentially with formula (II) is another reaction of these groups. A compound must be used to achieve this, which reacts with Z, though not with $R^1$. For the event that the free groups Z are hydroxy groups, an anhydride, for example, can be used for this, as the following example demonstrates:

The silicic acid polycondensates pursuant to the invention can be hardened in various manners. Thus, the existing C=C double bonds can be introduced to a cross-linking through a polyaddition with thiols and amines or a polymerization reaction through the formation of propagating carbon chains, which causes the material to harden. The condensates can also be hardened by other cross-linking reactions, e.g. through a reaction with di-, tri- or tetra-isocyanates, which connect to free carboxylic acid or hydroxy groups, or respectively multifunctional anhydrides for the reaction of condensates containing hydroxy groups, through which another, purely organic cross-link also arises.

The resin systems (i.e. the silicic acid polycondensates) of the present invention or their hardened products can be used for a number of applications, including in particular dental purposes, preferably for direct/indirect restorations, prophylaxis (e.g. through fissure sealing), prosthetics, and tooth replacement.

In the following, the invention is explained in further detail based on specific examples of reactions:

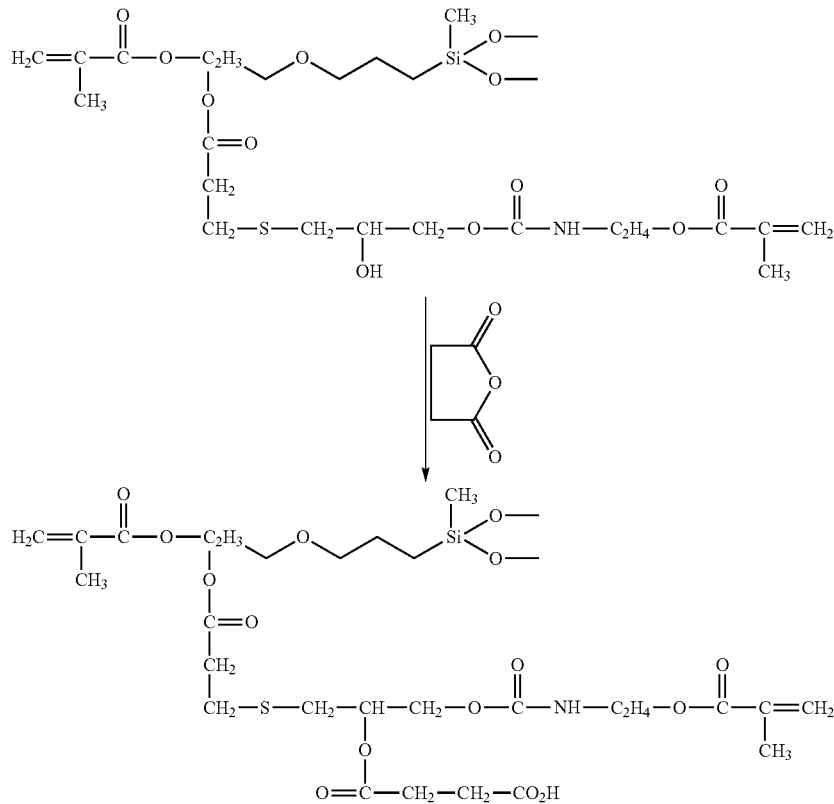

Instead, this additional reaction with a compound (V) can be conducted with a formula Y"W(Q)$_c$, wherein Y" represents NCO, epoxy or COA' with A'=hydroxy, a halogenide or —OC(O)$R^4$ with $R^4$=non-substituted or substituted hydrocarbon radical and W, Q, and c are defined above as for compound (III).

Together with this reaction, a reactive group is in turn likewise shifted to a spot further out in the molecule, wherein, however, the group $R^1$ remains untouched.

Example 1

Synthesis of the Base Resin System I (State of the Art)

For receiving 125.0 g (0.503 mol) of 3-Glycidyloxypropyltrimethoxysilane, triphenylphosphine (as a cat.), BHT (as a stabilizer), and then 47.35 g (0.550 mol) of methacrylic acid are added drop-wise in a dry atmosphere and stirred at 80° C. (approx. 24 hrs.). The reaction can be traced by the decline in carboxylic acid concentration via acid titration as well as the epoxy conversion via a Raman spectroscopy/epoxy titration.

The band of epoxy silane characteristic for the epoxy group appears in the Raman spectrum at 1256 cm$^{-1}$. The epoxy or carboxylic acid conversion is at ≥99% or ≥89% (→due to 1:1.1 carboxylic acid surplus). After adding acetic ester (1000 ml/mol of silane) and $H_2O$ for hydrolysis with HCl as cat., stir at 30° C. The progress of hydrolysis is respectively followed via water titration. Processing occurs after approx. multiple days of stirring through repeated extraction with aqueous NaOH and with water and filtration via hydrophobized filters. A rotary evaporator is used first and then an oil pump vacuum is used for suctioning. This resulted in a liquid resin without the use of reactive thinners (monomers) with a very low viscosity of approx. 3-6 Pa·s at 25° C. (heavily dependent upon exact hydrolysis and processing conditions) and 0.00 mmol of $CO_2H/g$ (no free carboxyl groups) as well as a refractive index $n_D$ of approx. 1.480.

Example 1a

For receiving 48.3 g (0.18 mol) from Base Resin System I and potentially 0.10 g of triethylamine, 5.50 g (0.051 mol) of thioglycerol (3-Mercaptopropan-1,2-diol) are added drop-wise while stirring. The reaction can be followed via NMR as well as through the decline of the HS bonds via Raman spectroscopy. The band characteristic for the HS group appears in the Raman spectrum at 2566 cm$^{-1}$. The result is a liquid resin with a viscosity of approx. 16-18 Pa·s at 25° C. (dependent upon the exact synthesis and processing conditions of the preliminary stages) and a refractive index $n_D$ of approx. 1.489. Additional processing is normally not necessary. The molar ratio of the deployed Base Resin System I to the product of the reaction with thioglycerol in the achieved resin is 1:0.282.

Example 1b

For receiving 37.2 g (0.14 mol) from Base Resin System I and potentially 0.16 g of a triethylamine, 8.54 g (0.079 mol) of thioglycerol (3-Mercaptopropan-1,2-diol) are added drop-wise while stirring. The result is a liquid resin with a viscosity of approx. 39 Pa·s at 25° C. and a refractive index $n_D$ of approx. 1.497. Additional processing is normally not necessary (see note for Example 2a). The molar ratio of the deployed Base Resin System I to the product of the reaction with thioglycerol in the achieved resin is 1:0.56.

The refractive index of this product can be finely adjusted through the share of thiol (see slight increase with respect to Base Resin System 1)

The polarity/hydrophily is adjustable through the OH content, which is introduced by the thiol compound as in this case via thioglycerol (i.e. heavy, graded increase compared to Base Resin System 1)

Example 2a

For receiving 13.09 g (0.040 mol) of a resin from example 1b and potentially 0.028 g of BHT, 3.48 g (0.0224 mol) of methacrylic acid isocyanatoethyl ester are added drop-wise while stirring in a dry atmosphere at 30° C. and continually stirred at 30° C. The reaction can be followed through the decline of the OCN band via the IR spectrum. The band characteristic for the OCN group appears in the IR spectrum at 2272 cm$^{-1}$. The result is a liquid resin with a viscosity of approx. 85 Pa·s at 25° C. (heavily dependent upon the exact synthesis and processing conditions, particularly the preliminary stages).

Example 2b

For receiving 13.09 g (0.040 mol) of a resin from example 1b and potentially 0.035 g of BHT, 6.59 g (0.0448 mol) of methacrylic acid isocyanatoethyl ester are added drop-wise while stirring in a dry atmosphere at 30° C. and continually stirred at 30° C. The result is a liquid resin with a viscosity of approx. 207 Pa·s at 25° C. (see note for 2a)

Example 2c

For receiving 9.82 g (0.030 mol) of a resin from example 1b and potentially 0.030 g BHT, 7.08 g (0.0456 mol) of methacrylic acid isocyanatoethyl ester are added drop-wise while stirring in a dry atmosphere at 30° C. and continually stirred at 30° C. The result is a liquid resin with a viscosity of approx. 207 Pa·s at 25° C. (see note for 2a).

Example 2d

For receiving 14.87 g (0.050 mol) of a resin from example 1a and potentially 0.030 g of BHT, 4.38 g (0.0282 mol) of methacrylic acid isocyanatoethyl ester are added drop-wise while stirring in a dry atmosphere at 30° C. and continually stirred at 30° C. The result is a liquid resin with a viscosity of approx. 43 Pa·s at 25° C. (see note for 2a).

Example 2e

For receiving 14.87 g (0.050 mol) of a resin from example 1a and potentially 0.040 g of BHT, 9.81 g (0.0632 mol) of methacrylic acid isocyanatoethyl ester are added drop-wise while stirring in a dry atmosphere at 30° C. and continually stirred at 30° C. The result is a liquid resin with a viscosity of approx. 167 Pa·s at 25° C. (see note for 2a).

Example 3

For receiving 20.81 g (0.070 mol) of a resin from example 1a, 16.83 g (0.109 mol) of methacrylic acid anhydride are added drop-wise while stirring in a dry atmosphere at 65° C. and continually stirred at 65° C. The reaction can be followed via NMR and the decline of the anhydride band can be followed via IR spectrum. The band characteristic for the anhydride group appears in the IR spectrum at 1785/1722 cm$^{-1}$. Following the usual processing for separating the methacrylic acid released during the addition as well as the extraction of the volatile components with the oil pump vacuum, a liquid resin emerges with a viscosity of approx. 8 Pa·s at 25° C. (heavily dependent upon the exact synthesis and processing conditions, particularly the preliminary stages).

TABLE 1

| Resin system | Breaking strength [MPa] | Modulus of elasticity [GPa] | Deflection [mm] | Contraction (15 min./ 1 day) [Vol.-%] |
|---|---|---|---|---|
| Base resin system I (comparison) | 83 | 1.5 | 2.9 | 5.2/5.8 |
| 2b | 120 | 2.60 | 3.20 | |
| 2c | 127 | 2.82 | 2.60 | |
| 2d | 107 | 2.30 | 3.26 | |
| 2e | 136 | 2.85 | 2.92 | 4.8/5.8 |
| 2f | 138 | 3.07 | 2.14 | |
| 3 | 103 | 2.32 | 2.35 | |

Example 4

For receiving 20.81 g (0.070 mol) of a resin from example 1a and 5.45 g of triethylamine (0.0501 mol) in 70 ml of THF as a solvent, 5.12 g (0.0455 mol) of methacrylic acid chloride are added drop-wise in a dry atmosphere and through cooling in an ice bath and continually stirred at room temperature. The reaction can be followed via NMR and the decline of the acid chloride band can be followed via IR spectrum. Following the usual processing for separating the amine hydrochloride produced during the addition as well as the extraction of the volatile components with an oil pump vacuum, a liquid resin emerges with a viscosity of approx. 6.9 Pa·s at 25° C.

Example 5

Synthesis of Base Resin System II (State of the Art)

For receiving 120.1 g (0.45 mol) from Base Resin System I (Example 1) and 35.1 g of triethylamine (0.347 mol) in 450 ml of THF as a solvent, 28.51 g (0.315 mol) of acrylic acid chloride are added drop-wise in a dry atmosphere and through cooling in an ice bath and continually stirred at room temperature. The reaction can be followed via NMR and the decline of the acid chloride band can be followed via IR spectrum. Following the usual processing for separating the amine hydrochloride produced during the addition as well as the extraction of the volatile components with an oil pump vacuum, a liquid resin emerges with a viscosity of approx. 1.5 Pa·s at 25° C. (heavily dependent upon the exact synthesis and processing conditions, particularly the preliminary stages).

Example 5a

For receiving 39.13 g (0.13 mol) from Base Resin System II and potentially 0.17 g of triethylamine, 9.00 g (0.0832 mol) of thioglycerol (3-Mercaptopropan-1,2-diol) are added. The reaction can be followed via NMR as well as through the decline of the HS bonds via Raman spectroscopy. The band characteristic for the HS group appears in the Raman spectrum at 2566 cm$^{-1}$. The result is a liquid resin with a viscosity of approx. 23 Pa·s at 25° C. (dependent upon the exact synthesis and processing conditions, particularly the preliminary stages). Additional processing is normally not necessary.

Example 6a

For receiving 16.47 g (0.045 mol) of a resin from example 5a (molar ratio=1:0.6) and potentially 0.021 g of BHT, 4.19 g (0.027 mol) of methacrylic acid isocyanatoethyl ester are added drop-wise while stirring in a dry atmosphere at 30° C. and continually stirred at 30° C. The reaction can be followed through the decline of the OCN band via the IR spectrum. The band characteristic for the OCN group appears in the IR spectrum at 2272 cm$^{-1}$. The result is a liquid resin with a viscosity of approx. 62 Pa·s at 25° C. (heavily dependent upon the exact synthesis and processing conditions, particularly the preliminary stages). Additional processing is normally not necessary.

Example 6b

For receiving 16.47 g (0.045 mol) of a resin from example 5a (molar ratio=1:0.6) and potentially 0.030 g of BHT, 8.38 g (0.054 mol) of methacrylic acid isocyanatoethyl ester are added drop-wise while stirring in a dry atmosphere at 30° C. and continually stirred at 30° C. The result is a liquid resin with a viscosity of approx. 164 Pa·s at 25° C. (see note for 6a).

TABLE 2

| Resin system | Breaking strength [MPa] | Modulus of elasticity [GPa] | Deflection [mm] |
| --- | --- | --- | --- |
| Base resin system II (comparison) | 79 | 1.74 | 1.98 |
| After the addition of thiol → Drastic increase of OH content | | | |
| 5a | 48 | 0.91 | 2.70 |
| After the addition of isocyanate methacrylate | | | |
| 6a | 122 | 2.53 | 2.90 |
| 6b | 132 | 2.95 | 2.40 |

Example 7a

For receiving 36.04 g (0.12 mol) from Base Resin System II, 5.41 g (0.072 mol) of 2-Methylamino-ethanol are slowly (exothermal reaction) added while stirring. The reaction can be followed via NMR. The result is a liquid resin with a viscosity of approx. 5 Pa·s at 25° C. (dependent upon the exact synthesis and processing conditions, particularly the preliminary stages). Additional processing is normally not necessary.

Example 8a

For receiving 12.44 g (0.036 mol) of resin from example 7a (molar ratio=1:0.5) and potentially 0.031 g of BHT, 2.79 g (0.018 mol) of methacrylic acid isocyanatoethyl ester are added drop-wise while stirring in a dry atmosphere at 30° C. and continually stirred at 30° C. The reaction can be followed through the decline of the OCN band via the IR spectrum. The band characteristic for the OCN group appears in the IR spectrum at 2272 cm$^{-1}$. The result is a liquid resin with a viscosity of approx. 15 Pa·s at 25° C. (heavily dependent upon the exact synthesis and processing conditions, particularly the preliminary stages). Additional processing is normally not necessary.

Example 8b

For receiving 11.74 g (0.034 mol) of resin from example 7a (molar ratio=1:0.7) and potentially 0.031 g of BHT, 3.69 g (0.0238 mol) of methacrylic acid isocyanatoethyl ester are added drop-wise while stirring in a dry atmosphere at 30° C. and continually stirred at 30° C. The result is a liquid resin with a viscosity of approx. 20 Pa·s at 25° C. Additional processing is normally not necessary (see note for 8a).

Example 8c

For receiving 5.00 g (0.0145 mol) of resin from example 7a (molar ratio=1:0.9) and potentially 0.014 g of BHT, 2.02 g (0.0130 mol) of methacrylic acid isocyanatoethyl ester are added drop-wise while stirring in a dry atmosphere at 30° C. and continually stirred at 30° C. The result is a liquid resin. Additional processing is normally not necessary (see note for 8a)

Example 9a

For receiving 60.1 g (0.20 mol) from Base Resin System II, 10.5 g (0.10 mol) of diethanolamine are slowly (exothermal reaction) added drop-wise while stirring. The reaction can be followed via NMR. The result is a liquid resin with a viscosity of approx. 9-12 Pa·s at 25° C. (dependent upon the exact synthesis and processing conditions, particularly the preliminary stages). Additional processing is normally not necessary. With 3.8/4.2 Vol.-% (15 min./1 day), the monomer-free resin system demonstrates a surprisingly low level of hardening shrinkage.

Example 10a

For receiving 10.59 g (0.030 mol) of resin from Example 9a and potentially 0.029 g of BHT, 3.72 g (0.024 mol) of methacrylic acid isocyanatoethyl ester are added drop-wise while stirring in a dry atmosphere at 30° C. and continually stirred at 30° C. The reaction can be followed through the decline of the OCN band via the IR spectrum. The band characteristic for the OCN group appears in the IR spectrum at 2272 cm$^{-1}$. The result is a liquid resin with a viscosity of approx. 39-45 Pa·s at 25° C. (heavily dependent upon the exact synthesis and processing conditions, particularly the preliminary stages). Additional processing is normally not necessary. With 4.0/4.8 Vol.-% (15 min./1 day), the monomer-free resin system demonstrates a surprisingly low level of hardening shrinkage.

Determination of the mechanical data as well as the hardening shrinkage:

Polymerization/hardening of various resin systems compared to the fundamental base resins:

The respective resin from the series of examples or the base resin systems ½ with % Lucirin TPO is added to a rod shape (2×2×25 mm$^3$). The (meth)acrylate groups are converted within the scope of a photo-induced radical polymerization, wherein the resin hardens. Using a 3-point bending test, the modulus of elasticity, the breaking strength, and deflection to the point of breakage of the resulting rods is determined after 1.5 days in storage at 40° C.

The shrinkage values are obtained using the buoyancy method within the scope of the photo-induced radical polymerization (15 min./1 day after exposure).

The examples allows us to see that, in a single materials base, a generally very broad spectrum of the modulus of elasticity is adjustable and clearly improved mechanical data (increased strength) is observed compared to the underlying base resin (state of the art). The systems can be implemented without the use of dental monomers, which is essential in light of increasing discussions about allergies in the dental field. The invention enables an additional functionality through the introduction of additional OH, or other groups. The products achieved in this manner have a surprisingly low shrinkage value.

What is claimed is:

1. A process for a chain extension of Si—C bonded radicals of silanes or siloxanes having at least two functional groups, wherein the number of functional groups on the respective Si—C bonded radicals is maintained or increased,
   wherein
   a silane or siloxane with a radical bonded to a silicon atom by a carbon atom, the radical bearing at least two functional groups,
   wherein a first group of the functional groups is an unsaturated, organically polymerizable group and a second group of said functional groups is selected among
   (a) additional unsaturated, organically polymerizable groups,
   (b) COOR$^8$ or —(O)$_b$P(O)(R$^5$)$_2$ and
   (c) —OH,
   with R$^8$ equal to R$^4$ or M$_{1/x}^{x+}$, M$^{x+}$ being hydrogen or an x-fold positively charged metal cation,
   and b=0 or 1,
   is converted in an initial reaction
   with a compound of a formula (I)

wherein
   X is SH, NH$_2$ or NHR$^4$,
   Z is OH, a carboxylic acid group —COOH or a salt or an ester of said group or a silyl group having formula SiX*$_3$ wherein the radicals X* represent a hydrocarbon radical,
   W is a substituted or non-substituted hydrocarbon group, a chain of which can be interrupted by
   —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, and
   a represents 1, 2, 3, 4 or a greater whole number, and
   wherein
   R$^4$ is a non-substituted or substituted hydrocarbon group,
   R$^5$ is a non-substituted or substituted hydrocarbon group or OR$^6$, and
   R$^6$ is hydrogen or is a non-substituted or substituted hydrocarbon group, such that the group X reacts with the first functional group.

2. Process according to claim 1, wherein Z is OH, the carboxylic acid group
   —COOH or a salt or an ester of said group.

3. Process according to claim 2, wherein the second of the functional groups of the radical bonded to a silicon atom of the silane or siloxane is an OH group.

4. Process according to claim 2, wherein the index a in the compound with said formula (I) represents 2, 3 or 4, and particularly 2.

5. Process according to claim 2, wherein X is SH, Z is OH, and a represents 2 or 3 in the compound with said formula (I).

6. Process according to claim 1, wherein a molar ratio of the first or all groups on the functional groups on the Si—C-bonded radicals to the groups Z in the compound with said formula (I) is >1 to 1, preferably being at least 1.05 to 1, and even more preferred being in the range of 1.05 to 1 to 1.50 to 1.

7. Process according to claim 2, wherein the product of said process is further reacted in a second reaction with a compound (II)

wherein Y is NCO, epoxy or, if the group or groups Z in the product of said process is/are (a) hydroxy group(s), COA',
   W is a substituted or non-substituted hydrocarbon group, a chain of which can be interrupted by
   —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—,
   R$^1$ is an unsaturated, organically polymerizable group,
   A' is hydroxy, a halogenide or —OC(O)R$^4$ with R$^4$ being a non-substituted or substituted carbon group,
   k=0 or 1, wherein k=0 is only possible in the event that Y represents COA', and
   b=1 or greater than 1,
   wherein the molar ratio of the product of the first reaction to the compound with formula (II) is preferably greater than 1, and more preferred being at least 1.05.

8. Process according to claim 7, wherein said process occurred with said compound (I), for which Z=OH, wherein compound (II) in the second reaction is used substoichiometrically with regard to the groups Z present in the product of the first reaction.

9. Process according to claim 2, wherein the product of said process is further converted in a second reaction, either with a compound (III)

$$Y'-W-(Q)_c \quad (III)$$

wherein

Y' is either is NCO, epoxy if the group or groups Z in the product of said process is/are (a) hydroxyl group(s), CAO', or, in the case of Z equal to COOH or a salt thereof, can instead have the meaning of $NHR^4$, $NH_2$, or OH with $R^4$=non-substituted or substituted hydrocarbon and, in the case of Z equal to OH, can have the meaning of COOH or a salt thereof, W is a substituted or non-substituted hydrocarbon group, a chain of which can be interrupted by
—S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, and Q is OH, $NR^7_2$, $NR^7_3{}^+$, $CO_2H$, $SO_3H$, $PO(OH)_2$ $PO(OR^4)_2$, $OPO(OH)_2$, $OPO(OR^4)_2$ or a salt of the previously mentioned acids, wherein $R^4$ has the above-specified meaning for said formula (I) and $R^7$ either has the same meaning as $R^4$ or two groups together can represent a potentially substituted or potentially unsaturated alkylene group, and c is 1, 2, 3, 4 or a greater number, or, wherein Y' and Q together form a group —C(O)O(O)C— and W is a straight-chain, branched or cyclic alkylene or alkenylene group, preferably with respectively 2 to 12 carbon atoms or an optionally alkyl-substituted or condensed arylene group, preferably with 6 to 12 carbon atoms, or, in the event that the group or groups Z in the product of the first reaction is/are (a) hydroxy group(s), is converted with $P_2O_5$ or with $POCl_3$, wherein the molar ratio of the product of the first reaction to the compound with formula (III) is preferably greater than 1, and more preferred being at least 1.05.

10. Process according to claim 7, wherein in said compound with the formula (II), Y is COA' and, in particular, is (meth)acrylic acid chloride or anhydride.

11. Process according to claim 7, wherein the product of the second reaction is further reacted in a third reaction with a compound (IV)

$$X-W-(Q)_c \quad (IV)$$

wherein X is SH, $NH_2$ or $NHR^4$ and W is a substituted or non-substituted hydrocarbon group, a chain of which can be interrupted by
—S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, Q is OH, $NR^7_2$, $NR^7_3{}^+$, $CO_2H$, $SO_3H$, $PO(OH)_2$ $PO(OR^4)_2$, $OPO(OH)_2$, $OPO(OR^4)_2$ or a salt of the previously mentioned acids, wherein $R^4$ has the above-specified meaning for said formula (I) and $R^7$ either has the same meaning as $R^4$ or two groups $R^7$ together can represent a potentially substituted or potentially unsaturated alkylene group, and c is 1, 2, 3, 4 or a greater number, wherein the molar ratio of the product of the second reaction to the compound with the formula (IV) is preferably greater than 1, and more preferred being at least 1.05.

12. Process according to claim 8, further comprising a reaction with a compound (V), which is selected from the group consisting of an anhydride of a dicarboxylic acid and a compound of a formula $Y''WC(Q)_c$, wherein Y" has the meaning of NCO, epoxy or COA' with A'=hydroxy, a halogenide or —OC(O)$R^4$ with $R^4$=a non-substituted or substituted hydrocarbon group, W is a substituted or non-substituted hydrocarbon group, a chain of which can be interrupted by
—S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, Q is OH, $NR^7_2$, $NR^7_3{}^+$, $CO_2H$, $SO_3H$, $PO(OH)_2$ $PO(OR^4)_2$, $OPO(OH)_2$, $OPO(OR^4)_2$ or a salt of the previously mentioned acids, wherein R has the above-specified meaning for said formula (I) and $R^7$ either has the same meaning as $R^4$ or two groups $R^7$ together can represent a potentially substituted or potentially unsaturated alkylene group, and c is 1, 2, 3, 4 or a greater number.

13. Process according to claim 7, wherein the product of the second reaction is further converted in a third reaction with a compound of said formula (I):

$$X-W-(Z)_a \quad (I)$$

wherein

X is SH, $NH_2$ or $NHR^4$,

Z is OH, a carboxylic acid group —COOH or a salt or an ester of said group or a silyl group, W is a substituted or non-substituted hydrocarbon group, a chain of which can be interrupted by
—S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, and a represents 1, 2, 3, 4 or a greater whole number, wherein $R^4$ is a non-substituted or substituted hydrocarbon group, $R^5$ is a non-substituted or substituted hydrocarbon group or $OR^6$, and $R^6$ is hydrogen or is a non-substituted or substituted hydrocarbon group, wherein the molar ratio of the product of the second reaction with said formula (I) in the third reaction is greater than 1, and preferably being at least 1.05.

14. Process according to claim 13, wherein the product of the process is further reacted in a fourth reaction either with a compound (III)

$$Y-W-(W)_c \quad (III)$$

wherein Y is NCO, epoxy or if the group or groups Z in the product of the first reaction is/are (a) hydroxy group(s) COA', W is a substituted or non-substituted hydrocarbon group, a chain of which can be interrupted by
—S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, Q is OH, $NR^7_2$, $NR^7_3{}^+$, $CO_2H$, $SO_3H$, $PO(OH)_2$, $PO(OR^4)_2$ or a salt of the aforementioned acids, wherein $R^4$ is a non-substituted or substituted hydrocarbon group, $R^7$ either has the same meaning as $R^4$ or two groups $R^7$ together represent an optionally substituted, optionally unsaturated alkylene group, and c is 1, 2, 3, 4 or a greater number, wherein the molar ratio of the product of the first reaction to the compound with said formula (II) is preferably greater than 1, and more preferably being at least 1.05, or, in the event that the group or groups Z in the product of the third reaction is/are (a) hydroxy group(s), is converted with $P_2O_5$ or $POCl_3$.

15. Process according to claim 13, wherein the product of the third reaction is further reacted in a fourth reaction with a compound having the formula (II), wherein the molar ratio of the product of the third reaction to the compound with said formula (II) is preferably greater than 1, and more preferably being at least 1.05.

16. Process according to claim 7, further comprising
    (a) the reaction of the respective product with a one or more multifunctional thiol, or
    (b) the polymerization of the respective product in a polyreaction, for which a part or all of the available reactive double bonds are integrated under the influence of heat, light, ionizing radiation or redox-induced in a propagating carbon chain.

17. Process according to claim 1, further comprising
    (a) the cross-linking of existing hydroxy or carboxylic acid groups with a di- or polyfunctional isocyanate, or
    (b) the cross-linking of existing hydroxy groups with a di- or polyfunctional, optionally activated, carboxylic acid.

18. Process according to claim 9, wherein in said compound with the formula (III), Y' is COA' and, in particular, is (meth)acrylic acid chloride or anhydride, or wherein Y'W(O)$_c$ is succinic anhydride, glutaric anhydride or maleic anhydride.

19. Process according to claim 15, further comprising
    (a) the reaction of the respective product with a one or more multifunctional thiol, or
    (b) the polymerization of the respective product in a polyreaction, for which a part or all of the available reactive double bonds are integrated under the influence of heat, light, ionizing radiation or redox-induced in a propagating carbon chain.

\* \* \* \* \*